US008190447B2

(12) United States Patent
Hungerford et al.

(10) Patent No.: US 8,190,447 B2
(45) Date of Patent: May 29, 2012

(54) COMPUTERIZED METHODS AND SYSTEMS FOR USER-CENTRIC SELECTION OF MENU ITEMS

(75) Inventors: Jill R. Hungerford, Kansas City, MO (US); Charles Cameron Brackett, Overland Park, MO (US); Daniel P. Devers, Kansas City, MO (US)

(73) Assignee: Cerner Innovation, Inc., Overland Park, KS (US)

( * ) Notice: Subject to any disclaimer, the term of this patent is extended or adjusted under 35 U.S.C. 154(b) by 1654 days.

(21) Appl. No.: 11/303,637

(22) Filed: Dec. 16, 2005

(65) Prior Publication Data

US 2006/0277066 A1     Dec. 7, 2006

Related U.S. Application Data

(63) Continuation-in-part of application No. 11/143,001, filed on Jun. 2, 2005.

(51) Int. Cl.
*G06Q 10/00* (2006.01)
*G06Q 50/10* (2006.01)

(52) U.S. Cl. ............................................. 705/2; 705/3
(58) Field of Classification Search ................. 705/2–3; 340/573.1; 235/462.45
See application file for complete search history.

(56) References Cited

U.S. PATENT DOCUMENTS

| | | | |
|---|---|---|---|
| 5,025,374 A | 6/1991 | Roizen et al. | |
| 5,072,383 A | 12/1991 | Brimm et al. | |
| 5,842,175 A | 11/1998 | Andros et al. | |
| 5,946,659 A | 8/1999 | Lancelot et al. | |
| 6,375,077 B1 * | 4/2002 | Hankins | 235/462.45 |
| 6,789,091 B2 | 9/2004 | Gogolak | |
| 7,076,436 B1 | 7/2006 | Ross, Jr. et al. | |
| 2001/0001144 A1 * | 5/2001 | Kapp | 705/3 |
| 2002/0046047 A1 | 4/2002 | Budd | |

(Continued)

FOREIGN PATENT DOCUMENTS

GB     2407891     6/2008

OTHER PUBLICATIONS

Final Office Action mailed Jan. 22, 2009 U.S. Appl. No. 11/143,001, filed Jun. 2, 2005.

(Continued)

*Primary Examiner* — Luke Gilligan
*Assistant Examiner* — Joseph Burgess
(74) *Attorney, Agent, or Firm* — Shook, Hardy & Bacon LLP

(57) ABSTRACT

Methods for use in, e.g., in-patient care computing environment, for user-centric (e.g., in-patient-centric) selection of at least one menu item are provided. A method in accordance with one embodiment of the present invention may include receiving a plurality of menu item identifiers, each menu item identifier being associated with a different menu item, associating the menu item identifiers with an electronic record associated with an in-patient, displaying the menu item identifiers on at least one patient-viewable display device, and receiving a user selection of at least one of the menu item identifiers. If desired, the method may additionally include filtering the menu item identifiers based on at least one criterion derived from the electronic record to create a set of filtered menu item identifiers and displaying the set of filtered menu item identifiers on the patient-viewable display device rather than the plurality of menu item identifier.

7 Claims, 17 Drawing Sheets

U.S. PATENT DOCUMENTS

| | | |
|---|---|---|
| 2002/0082865 A1 | 6/2002 | Bianco et al. |
| 2002/0198876 A1 | 12/2002 | Zielinski et al. |
| 2003/0052787 A1* | 3/2003 | Zerhusen et al. .......... 340/573.1 |
| 2003/0069759 A1 | 4/2003 | Smith |
| 2003/0163535 A1 | 8/2003 | Suzuki |
| 2004/0049407 A1* | 3/2004 | Rosenberg ........................ 705/2 |
| 2004/0081641 A1 | 4/2004 | Kim et al. |
| 2005/0080650 A1* | 4/2005 | Noel ................................. 705/2 |
| 2005/0125255 A1 | 6/2005 | Mockett |
| 2006/0047538 A1 | 3/2006 | Condurso et al. |
| 2006/0178913 A1 | 8/2006 | Lara et al. |

OTHER PUBLICATIONS

Final Office Action mailed Jun. 24, 2010 U.S. Appl. No. 11/143,001, filed Jun. 2, 2005.

Non-Final Office Action mailed Jun. 23, 2008 U.S. Appl. No. 11/143,001, filed Jun. 2, 2005.

Non-Final Office Action mailed Aug. 03, 2009 U.S. Appl. No. 11/143,001, filed Jun. 2, 2005.

* cited by examiner

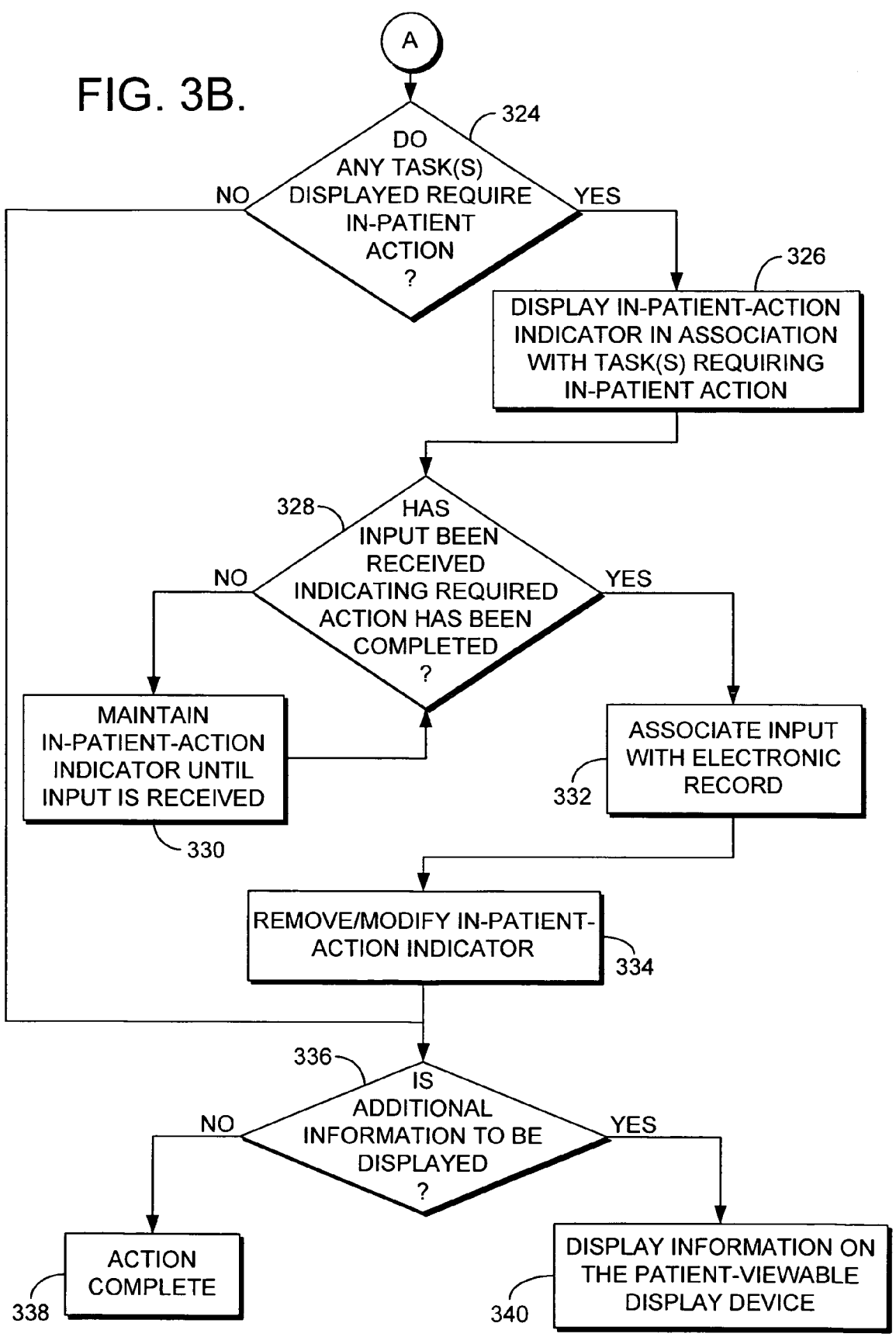

COMPUTERIZED METHODS AND SYSTEMS FOR USER-CENTRIC SELECTION OF MENU ITEMS

CROSS-REFERENCE TO RELATED APPLICATIONS

This application is a continuation-in-part of prior application Ser. No. 11/143,001, filed Jun. 2, 2005.

STATEMENT REGARDING FEDERALLY SPONSORED RESEARCH OR DEVELOPMENT

Not Applicable.

TECHNICAL FIELD

The present invention relates to computing environments. More particularly, embodiments of the present invention relate to methods and systems for use in, e.g., an in-patient care computing environment, the methods and systems for user-centric (e.g., in-patient-centric) selection of at least one menu item.

BACKGROUND

In modern clinical settings, there is often an electronic record, e.g., an electronic medical record, associated with each patient presenting at a patient care institution, for example, a hospital or clinic. One example of such an electronic record is an electronic medical record, such as the POWERCHART application available from Cerner Corporation of North Kansas City, Miss. Electronic medical records are designed to offer a single location wherein as much information as possible relevant to the patient with whom the record is associated is readily viewable and actionable, generally by a clinician or other authorized institution personnel.

As information is manually entered into a patient's medical record, or the medical record is automatically populated based on information received from an associated system, events directly affecting the patient's schedule, for instance, tasks, may be generated. "Tasks" are generally used by a clinician or other care giver and serve as reminders that something was, or is, to be done for a particular patient, as well as what was, or is, to be done. That is, "tasks" are typically reminders to the clinician that, for instance, a medication was, or is, to be given, a vital sign was, or is, to be checked, data was, or is, to be collected, a procedure was, or is, to be performed, or the like. Tasks generally have a time associated therewith which may be a particular instance in time or may indicate that the task is continuous, e.g., an IV medication administered over a period of several hours, and specify only an initiation time and/or monitoring time. Alternatively, if desired, a time associated with a task may indicate that a task is to be performed only as needed (i.e., PRN).

Tasks are typically generated from clinical orders and specify, with particularity, what is to be done for a patient. Thus, if an order states that a patient is to receive four 20 mg doses of medication X, one dose every three hours beginning at 12:00 pm, four tasks may be generated for the patient: a first task at 12:00 pm, a second tasks at 3:00 pm, a third task at 6:00 pm, and a fourth task at 9:00 pm, each task indicating that 20 mg of medication X are to be administered.

While this information is generally viewable by the clinician and other authorized institution personnel, the electronic medical record is typically not made available to the patient for viewing. Thus, referring back to the above-described example, although the order setting forth the administration schedule of medication X is known to relevant institution personnel, the patient remains unaware that s/he has particular events scheduled throughout his or her day at 12:00 pm, 3:00 pm, 6:00 pm, and 9:00 pm. In fact, the patient may not be aware that the medication administration has been scheduled for a particular time until the appropriate institution personnel arrives at his or her room to carry out the administration.

This overall unawareness of what is to take place throughout the day can make patients feel out of control and detached from the care they are receiving. In-patient stays in clinical institutions can be nerve-wracking experiences for many individuals and simple knowledge of what's to come in the next few hours can aid dramatically in easing a patient's mind. Further, when unaware of their daily schedules, patients often do not feel at ease to schedule events of their own. For instance, if a particular friend or family member wishes to come to the clinic and visit the patient, the patient is unaware of what might be a good time to instruct the friend or family member to arrive. Still further, if the patient wishes to take a nap or spend some time reading a new book, s/he may get five minutes into it only to find out something else has been scheduled for the same time frame. Events such as this can be extremely frustrating and contribute to overall discontent with a patient's stay at the institution.

Another source of patient discontent with in-patient stays in clinical institutions is often the meal selection process, or lack thereof. Typically, meal planning is minimally integrated into the overall in-patient care continuum. Rather, meal planning is primarily a manual process with little to ensure safety as a primary care concern, that is, with little to validate meal orders against an in-patient's relevant medical information. For instance, a in-patient who is not permitted to participate in his or her meal selection may be lactose intolerant and yet offered only milk as a lunch beverage. This causes the in-patient to have to contact the appropriate personnel to get the milk taken away and something else brought to them. Often times this exchange is not associated with the in-patient's electronic record and, accordingly, when the dinner meal is delivered, the same process must take place.

Alternatively, an in-patient who is permitted to participate in his or her meal selection may choose a menu item that, unbeknownst to them, is contra-indicated due to a particular medication the in-patient may be taking. In this instance, delivery of the chosen menu item selection could have serious consequences to the in-patient.

Accordingly, a system and method which permits an in-patient to actively participate in his or her meal selection and which associates those meal choices with the in-patient's electronic record would be desirable. Additionally, a system and method which verifies an in-patient's meal selections against the in-patient's relevant medical information would be advantageous.

BRIEF SUMMARY

Embodiments of the present invention relate to methods for use in, e.g., an in-patient care computing environment, for user-centric (e.g., in-patient-centric) selection of at least one menu item. In one embodiment, the method includes receiving a plurality of menu item identifiers, each menu item identifier being associated with a different menu item, associating the plurality of menu item identifiers with an electronic record associated with an in-patient, displaying the plurality of menu item identifiers on at least one patient-viewable display device, and receiving a user selection (e.g., an in-patient selection) of at least one of the plurality of menu item identifiers. If desired, the method may further include filtering the plurality of menu item identifiers based on at least one criterion derived from the electronic record to create a set of filtered menu item identifiers and displaying the set of filtered menu item identifiers on the patient-viewable display device rather than the plurality of menu item identifiers.

In other embodiments, the method may include comparing user-selected menu item identifiers with at least one criterion derived from the electronic record to determine if any of the menu items associated with the selected menu item identifiers are contra-indicated for the in-patient with whom the electronic record is associated. If any of the menu items associated with the selected menu item identifiers is contra-indicated, the method may further include displaying an alert on the patient-viewable display device in association with the appropriate menu item identifier.

In another embodiment, a method in accordance with the present invention includes receiving at least one menu item identifier, the menu item identifier being associated with a menu item, associating the at least one menu item identifier with an electronic record associated with an in-patient, filtering the at least one menu item identifier based on at least one criterion derived from the electronic record to create at least one filtered menu item identifier, and displaying the at least one filtered menu item identifier on at least one patient-viewable display device. If desired, the method may further include receiving a user selection of at least one filtered menu item identifier from a set of filtered menu item identifiers and associating the user selection with the electronic record associated with the in-patient.

The present invention additionally relates to one or more computer-readable media having computer-executable instructions for performing the methods set forth herein, as well as to computers programmed to perform the disclosed methods.

Additional embodiments of the present invention relate to systems for use in, e.g., an in-patient care computing environment, for user-centric (e.g., in-patient-centric) selection of at least one menu item. In one embodiment, the system may include a menu item identifier receiving module for receiving a plurality of menu item identifiers, each menu item identifier being associated with a different menu item, an associating module for associating the plurality of menu item identifiers with an electronic record associated with an in-patient, a displaying module for displaying the plurality of menu item identifiers on at least one patient-viewable display device, and a user selection receiving module for receiving a user selection of at least one of the plurality of menu item identifiers. If desired, the system may further include a filtering module for filtering the plurality of menu item identifiers based on at least one criterion derived from the electronic record to create a set of filtered menu item identifiers.

In other embodiments the system may include a comparing module for comparing the at least one of the plurality of menu item identifiers with at least one criterion derived from the electronic record to determine if the menu item associated with the at least one of the plurality of menu item identifiers is contra-indicated for the in-patient with whom the electronic record is associated. If it is determined that the at least one of the plurality of menu item identifiers is contra-indicated, the method may further include an alert displaying module for displaying an alert on the patient-viewable display device in association with the appropriate menu item identifier.

In another embodiment, a system in accordance with the present invention includes a menu item receiving module for receiving a plurality of menu item identifiers, each menu item identifier being associated with a different menu item, a first associating module for associating the plurality of menu item identifiers with an electronic record associated with an in-patient, a filtering module for filtering the plurality of menu item identifiers based on at least one criterion derived from the electronic record to create a set of filtered menu item identifiers, and a displaying module for displaying the set of filtered menu item identifiers on at least one patient-viewable display device. If desired, the system may further include a user selection receiving module for receiving a user selection of at least one filtered menu item identifier from the set of filtered menu item identifiers and a second associating module for associating the user selection of the at least one filtered menu item identifier with the electronic record associated with the in-patient.

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE SEVERAL VIEWS OF THE DRAWINGS

The present invention is described in detail below with reference to the attached drawing figures, wherein:

FIGS. 3A and 3B are a flow diagram showing a more detailed method for displaying clinically-related in-patient information than the method of FIG. 2 in accordance with an embodiment of the present invention;

FIG. 6A is an exemplary screen display illustrating display of clinically-related in-patient information on a patient-viewable display device, in accordance with an embodiment of the present invention;

FIG. 6B is an exemplary screen display similar to that shown in FIG. 6A and additionally illustrating live-connect functionality through an audio/video connection, in accordance with an embodiment of the present invention;

FIG. 8A is an exemplary screen display illustrating a dialog box for selecting at least one menu item from a list of menu item options in accordance with an embodiment of the present invention;

FIG. 8B is an exemplary screen display illustrating that a user has selected a plurality of menu items from the list of options shown in the screen display of FIG. 8A, such selected menu items being displayed in the scratch pad portion of the dialog box, in accordance with an embodiment of the present invention;

FIG. 8C is an exemplary screen display illustrating alerts that may be displayed in association with contra-indicated selected menu items in accordance with an embodiment of the present invention;

FIG. 8D is an exemplary screen display illustrating that upon user acceptance of contra-indicated menu items, such items may be displayed as a planned meal in accordance with an embodiment of the present invention;

FIG. 8E is an exemplary screen display illustrating the planned meal of FIG. 8D being displayed in the menu display area of a patient-viewable display device in accordance with an embodiment of the present invention;

FIG. 8F is an exemplary screen display illustrating that upon user rejection of contra-indicated menu items, such items may be removed from the list of selected items shown in the scratch pad portion of the dialog box in accordance with an embodiment of the present invention;

FIG. 8G is an exemplary screen display illustrating that a user, after rejection of the contra-indicated menu items, has selected a different set of menu items in response to the displayed alerts shown in FIG. 8C in accordance with an embodiment of the present invention;

FIG. 8H is an exemplary screen display illustrating that upon verification, if there are no contra-indicated menu items selected, the selected menu items may be displayed as a planned meal in accordance with an embodiment of the present invention; and FIG. 8I is an exemplary screen display illustrating the planned meal of FIG. 8H being displayed in the menu display area of a patient-viewable display device in accordance with an embodiment of the present invention.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

The present invention provides a computerized method and system for displaying clinically-related in-patient information on at least one patient-viewable display device. As used herein, the terms "individual", "person", "patient", and "in-patient" are used interchangeably and are not meant to limit the nature of the referenced individual in any way. Rather, the methods and systems described herein are equally applicable in, for instance, a veterinary setting. Further, use herein of the term "patient" and/or "in-patient" is not meant to imply any particular relationship between the individual in question and those accessing, updating, and/or viewing the patient's information (e.g., the patient's meal selection information).

Additionally, as used herein, the term "patient-viewable display device" refers to a display device viewable by the in-patient, the in-patient's friends, and/or family members of the in-patient, and the like. The term "patient-viewable display device" is thus not intended to imply that the information must be viewable by the individual to whom the information pertains, although such is contemplated by some embodiments of the present invention. The term "patient-viewable display device" is also not intended to imply that the display device must be in proximity to the in-patient. In fact, embodiments of the present invention contemplate that information pertaining to the individual in question may be viewable by individuals outside of the institution, for instance, the information may be viewable by a family member at his or her place of residence. All such variations are contemplated within the term "patient-viewable display device", as that term is utilized herein. In one embodiment, the patient-viewable display device is a flat panel monitor having an interactive touch screen located in proximity to the in-patient and readily available to, e.g., the in-patient and the in-patient's friends and/or family members, at all times.

Having provided a brief overview of embodiments of the present invention, an exemplary operating environment for embodiments of the present invention is described below.

Figure 1:
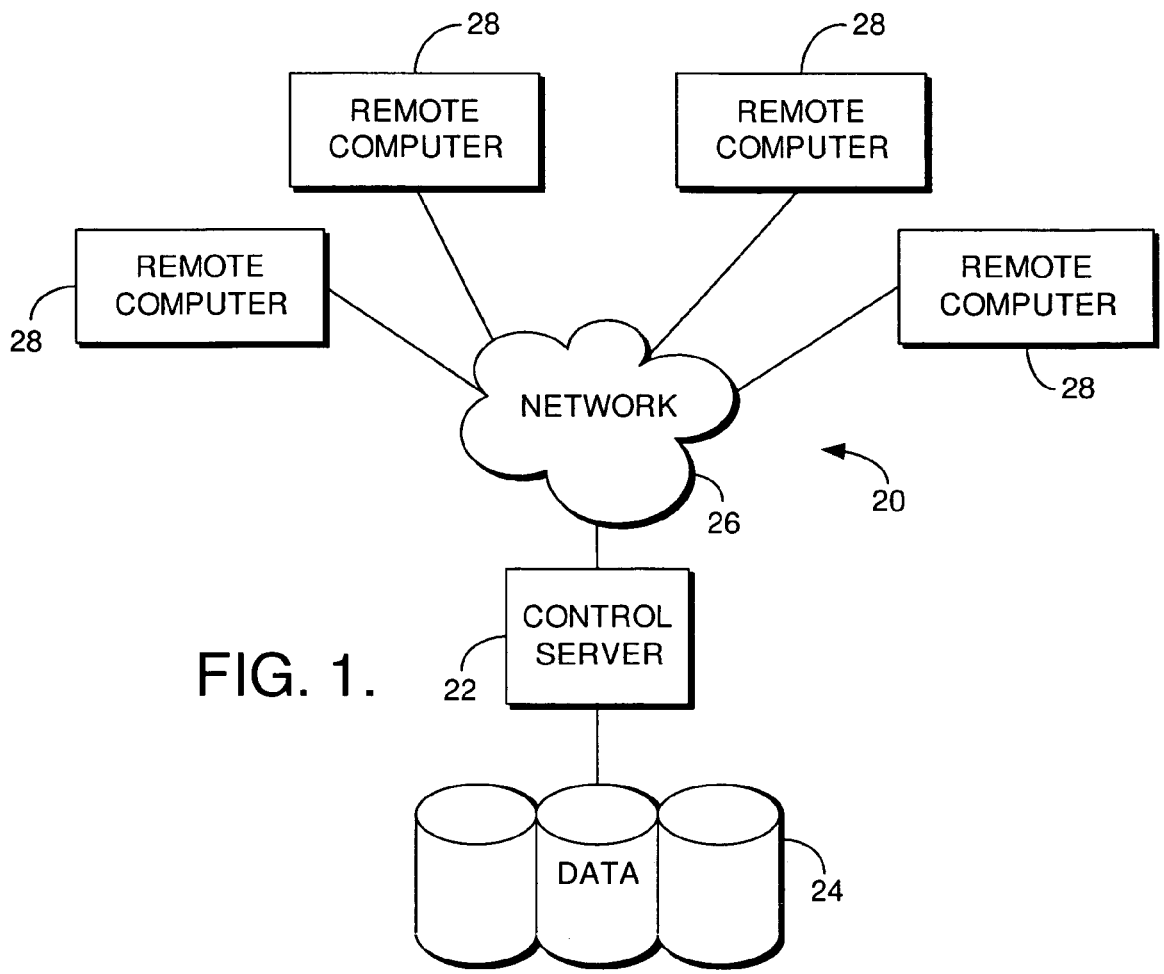
FIG. 1 is a block diagram of an exemplary computing environment suitable for use in implementing the present invention.

Referring to the drawings in general, and initially to FIG. 1 in particular, an exemplary computing system environment, for instance, a medical information computing system, on which the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

Embodiments of the present invention may be operational with numerous other general purpose or special purpose computing system environments or configurations. Examples of well-known computing systems, environments, and/or configurations that may be suitable for use with embodiments of the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

Embodiments of the present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 20 includes a general purpose computing device in the form of a control server 22. Components of the control server 22 may include, without limitation, a processing unit, internal system memory, and a suitable system bus for coupling various system components, including database cluster 24, with the control server 22. The system bus may be any of several types of bus structures, including a memory bus or memory controller, a peripheral bus, and a local bus, using any of a variety of bus architectures. By way of example, and not limitation, such architectures include Industry Standard Architecture (ISA)

bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 22 typically includes therein, or has access to, a variety of computer readable media, for instance, database cluster 24. Computer readable media can be any available media that may be accessed by control server 22, and includes volatile and nonvolatile media, as well as removable and non-removable media. By way of example, and not limitation, computer readable media may include computer storage media and communication media. Computer storage media may include, without limitation, volatile and nonvolatile media, as well as removable and non-removable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by control server 22. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its characteristics set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 24, provide storage of computer readable instructions, data structures, program modules, and other data for control server 22.

The control server 22 may operate in a computer network 26 using logical connections to one or more remote computers 28. Remote computers 28 may be located at a variety of locations in a medical or research environment, for example, but not limited to, clinical laboratories, hospitals and other in-patient settings, veterinary settings, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 28 may also be physically located in non-traditional medical care environments so that the entire health care community may be capable of integration on the network. The remote computers 28 may be personal computers, servers, routers, network PCs, peer devices, other common network nodes, or the like, and may include some or all of the components described above in relation to the control server 22. The devices can be personal digital assistants or other like devices.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the control server 22 may include a modem or other means for establishing communications over the WAN, such as the Internet. In a networked environment, program modules or portions thereof may be stored in the control server 22, in the database cluster 24, or on any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., control server 22 and remote computers 28) may be utilized.

In operation, a user may enter commands and information into the control server 22 or convey the commands and information to the control server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the control server 22. In addition to a monitor, the control server 22 and/or remote computers 28 may include other peripheral output devices, such as speakers and a printer.

Although many other internal components of the control server 22 and the remote computers 28 are not shown, those of ordinary skill in the art will appreciate that such components and their interconnection are well known. Accordingly, additional details concerning the internal construction of the control server 22 and the remote computers 28 are not further disclosed herein.

Although methods and systems of embodiments of the present invention are described as being implemented on a WINDOWS operating system, operating in conjunction with an Internet-based system, one of ordinary skill in the art will recognize that the described methods and systems can be implemented in any system supporting the receipt and processing of healthcare orders. As contemplated by the language above, the methods and systems of embodiments of the present invention may also be implemented on the standalone desktop, personal computer, or any other computing device used in a healthcare environment or any of a number of other locations.

As previously mentioned, embodiments of the present invention relate to methods for use in, e.g., an in-patient care computing environment, for displaying clinically-related in-patient information on at least one patient-viewable display device. The term "clinically-related in-patient information" as utilized herein, refers to information which is derived from clinical information that has been associated with the in-patient in question. That is, the information to be displayed has particular relevance to the in-patient as it has been selected for display on the basis of clinical information associated with the in-patient. Thus, the information is not randomly selected for display but is information directly affecting, or otherwise of particular interest to, the individual in question.

Figure 2:
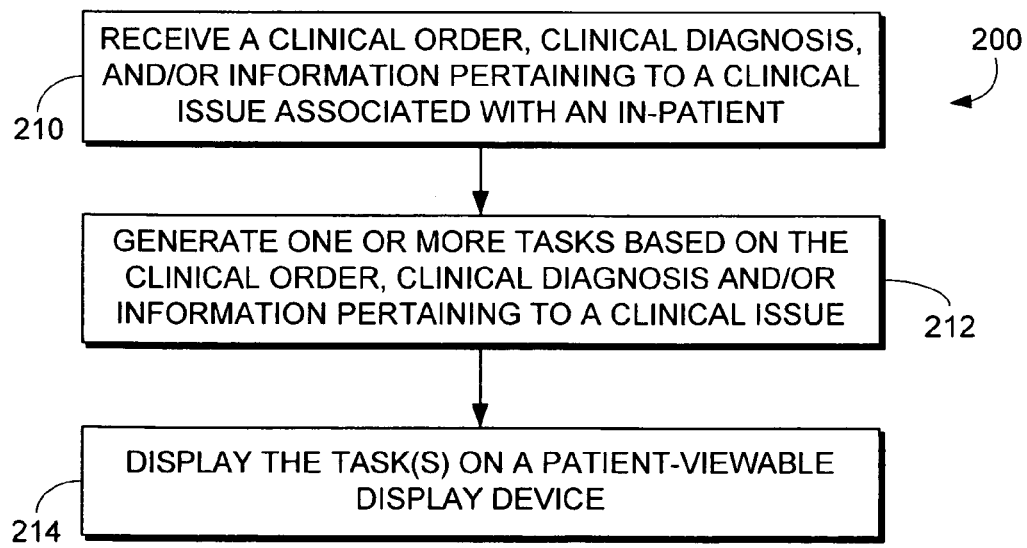
FIG. 2 is a flow diagram showing a method for displaying clinically-related in-patient information in accordance with an embodiment of the present invention.

With reference to FIG. 2, a flow diagram representative of a method for displaying such clinically-related in-patient information in accordance with an embodiment of the present invention is illustrated and depicted generally as reference numeral 200. Method 200 may be implemented on the above-described exemplary computing system environment (FIG.

1) and, by way of example only, may be utilized by an in-patient in a patient care institution to view his or her daily schedule.

Initially, as indicated at block 210, a clinical order, clinical diagnosis, and/or information pertaining to a clinical issue associated with an in-patient is received. Next, as indicated at block 212, one or more tasks are generated based on the clinical order, clinical diagnosis, and/or information pertaining to the clinical issue received. The concept of tasks generated from a clinical order was discussed herein above and may include, by way of example only, a schedule of administration for a particular medication. Typically, clinical orders are thought of as being created by a physician or other appropriate care-giver. However, as the term "clinical order" is utilized herein, an order may also be created by the in-patient. For instance, if an in-patient desires to have the temperature in his or her room decreased at 9:00 pm for more comfortable slumber, s/he may create an order for a room temperature alteration that can cause display of a task to decrease the temperature at 9:00 pm. As all information displayed on the patient-viewable display device, as more fully described below, is also made accessible to the appropriate institution personnel, and as this is likely something the in-patient cannot do him or herself, the appropriate institution personnel can see the task generated from the in-patient-created order and can perform the task at the designated time.

Tasks generated based upon a clinical diagnosis may include, by way of example only, a schedule of tests that are routinely run upon verification of a particular diagnosis, and the like. Tasks generated based upon information pertaining to a clinical issue similarly may include, by way of example only, a schedule of tests that are routinely run upon presentation of a patient with a particular set of symptoms that may be indicative of any number of disparate diagnoses.

Subsequently, as indicated at block 214, the task(s) generated based on the clinical order, clinical diagnosis, and/or information pertaining to a clinical issue associated with an in-patient may be displayed on at least one patient-viewable display device, that is, a computing device monitor, display screen, or the like. The task(s), and any additional information (as more fully described below) may be viewable on multiple display devices, for instance, a display device located in a patient's room, a display device located in an institution waiting area, and/or a display device located at any location remote from the in-patient and/or institution. For instance, in one specific example, the patient-viewable information may be available for viewing on a display device located overseas by military personnel as s/he attempts to monitor the care being received by a loved one.

Additionally, the information displayed may be continuously updated in real-time so that the displayed information changes as care progresses. Accordingly, the in-patient and his or her loved ones may be assured that they are at all times up to speed on the in-patient's care.

Figure 3A:
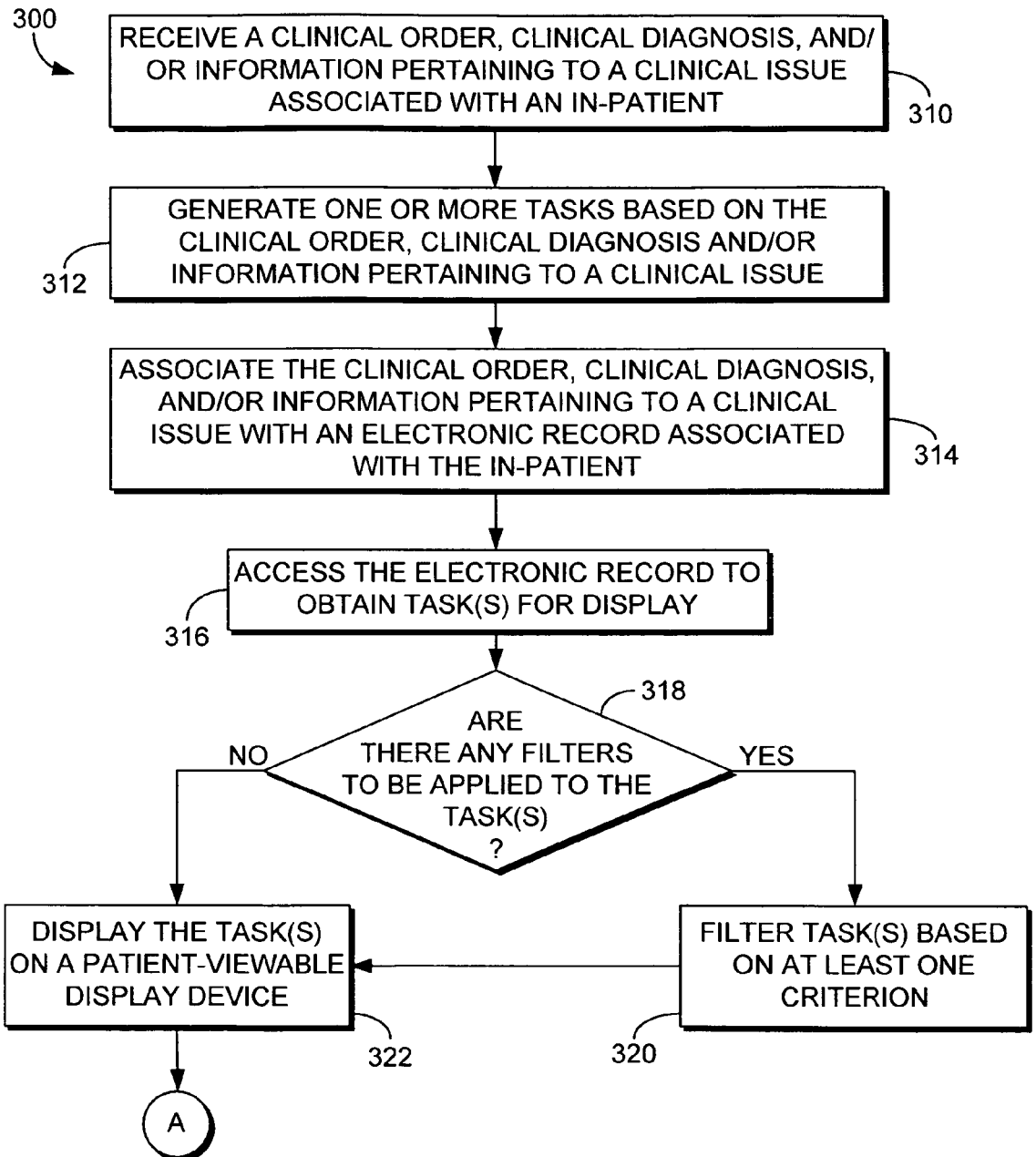

With reference to FIGS. 3A and 3B, a flow diagram is illustrated which shows a more detailed method 300 for displaying clinically-related in-patient information on at least one patient-viewable display device than that shown in FIG. 2. Initially, as indicated at block 310, a clinical order, clinical diagnosis, and/or information pertaining to a clinical issue associated with an in-patient is received. Next, as indicated at block 312, one or more tasks are generated based on the clinical order, clinical diagnosis, and/or information pertaining to the clinical issue received. Each of steps 310 and 312 was discussed more fully herein above with reference to steps 210 and 212, respectively, of FIG. 2.

Subsequently, as indicated at block 314, the clinical order, clinical diagnosis, and/or information pertaining to a clinical issue associated with the in-patient is associated with an electronic record associated with the in-patient, e.g., an electronic medical record, such as the POWERCHART application available from Cerner Corporation of North Kansas City, Miss. By providing association with an electronic record, all information displayed (as more fully described below) may be automatically updated in real-time, providing up-to-the-minute relevant information to in-patients and their loved ones.

Next, as indicated at block 316, the electronic medical record is accessed to obtain tasks for display. In one embodiment, all tasks generated at the step indicated at block 312 initially may be accessed.

It is next determined whether or not there are any filters to be applied to the task(s) obtained. This is indicated at block 318. Filters may include, by way of example only, filtering criteria specified by a care-giver, filtering criteria specified by the in-patient, and/or filtering criteria specified by the institution. A care-giver-specified filtering criterion may be, by way of example only, an instruction that procedures automatically scheduled on the basis of a particular lab test result not be made available for display until specifically directed by the care-giver, such instruction being provided only subsequent to the lab test result being explained to the patient. An in-patient-specified criterion may be, by way of example only, an instruction that the patient wishes only to be informed of those tasks which cause interruption to the patient and not of those tasks which may be performed by institution personnel without the patient being disturbed. An institution-specified criterion may be, by way of example only, an instruction that all patients scheduled to undergo surgical procedures be informed of the risks associated with such procedures prior to the procedure being displayed on the patient's schedule.

If it is determined at the step indicated at block 318 that one or more filters are to be applied to the task(s) obtained, the filters are subsequently applied and the task(s) are filtered based upon at least one criterion. This is indicated at block 320. Subsequently, or if it is determined that no filters are to be applied to the task(s) obtained, the task(s) are displayed on at least one patient-viewable display device, as indicated at block 322.

Turning now to FIG. 3B, it is next determined whether any of the task(s) displayed require in-patient action. This is indicated at block 324. By way of example only, in order for an institution to perform certain surgical procedures, the in-patient must be made aware of the risks associated with the procedure and execute a consent therefore. In this instance, a task stating, e.g., "Read and Sign Consent" may be generated and completion of such task may be required prior to the surgical procedure taking place. If it is determined that a particular task requires in-patient action, an in-patient-action indicator may be displayed in association with the task, as indicated at block 326. An exemplary in-patient-action indicator is shown and described more fully below with reference to FIG. 6A.

If an in-patient-action indicator has been displayed in association with a particular task, it is next determined whether input has been received indicating that the in-patient-required action has been completed. This is indicated at block 328. That is, referring to the above-described "Read and Sign Consent" task, it may be determined whether input has been received which indicates that such consent has been executed. If such input has not been received, the in-patient-action indicator is maintained in association with the task which requires action until such input is received, as indicated at block 330. However, if input is received which indicates that the required action has been completed, such input is subsequently associated with the electronic record associated with the in-patient, e.g., the electronic medical record. This is indicated at block 332. In this way, the care giving institution may track compliance with certain regulatory requirements with increased ease.

Additionally, in one embodiment, input may be received which indicates that a particular patient or his/her representative has refused to execute a requested consent or that a previously executed consent has been modified or canceled. As the input is integrated with an electronic record associated with the in-patient, if such modification, cancellation, or refusal input is received, the relevant clinician and/or other institution personnel may be automatically notified and/or the consent may be automatically identified as no longer effective as originally executed. Further, any procedures which have already been scheduled may be canceled pending receipt of the appropriate consent with or without accompanying notice to the relevant clinician and/or other institution personnel.

The in-patient-action indicator may subsequently be removed from association with the task which required in-patient action or may be modified to indicate that the required action has been completed, as indicated at block 334.

If it is determined that no displayed tasks require in-patient action, or upon removal or modification of the in-patient-action indicator for any tasks for which in-patient action was required, it is subsequently determined whether any additional information is to be displayed. This is indicated at block 336. Additional information may include additional clinically-related information, such as, by way of example only, educational materials explaining procedures scheduled to be performed for the in-patient or setting forth the potential side effects of medications the in-patient is scheduled to receive, educational materials mandated by Joint Commission on Accreditation of Healthcare Organizations (JCAHO) requirements, support group information, patient surveys, and/or selectable links thereto.

In one embodiment, the electronic record associated with the in-patient may also be integrated with the institution's billing system, e.g., the PROFIT system available from Cerner Corporation of North Kansas City, Miss. If such integration exists, additional information may further include a summary or itemized listing of charges the in-patient has incurred during their stay, such charge-related information being displayed, e.g., a pre-determined number of hours prior to the in-patient's discharge from the institution. Alternatively, charge-related information may be displayed as a task which may or may not require in-patient action, e.g., review and/or acceptance or modification prior to discharge.

Additional information may also include information which the in-patient may be interested in but which is not clinically-related, for instance, institution visiting hours or chapel service schedules, email communications, electronic messages, meal menu choices, and selectable links thereto. Methods and systems related to meal menu choices and user-centric (e.g., in-patient-centric) selection thereof are more fully described below with reference to FIGS. 7A, 7B and 8A-8I.

If it is determined that no additional information is to be displayed, action is complete, as indicated at block 338. If it is determined that additional information is to be displayed, such additional information is subsequently displayed on the patient-viewable display device, as indicated at block 340.

It will be understood and appreciated by those of ordinary skill in the art that the steps indicated at block 336, 338 and 340 may be performed at any time during the method set forth in FIGS. 3A and 3B and that waiting, for instance, until decisions on in-patient-action items have been resolved is optional and not intended to limit the present invention in any way. For instance, additional information may be displayed contemporaneously with display of tasks on the patient-viewable display device or may be displayed prior to or independently of any tasks being received, if desired. Additionally, determinations regarding display of additional information may be performed multiple times as additional inputs and/or changes in displayed information become available. All such variations are contemplated to be within the scope hereof.

Figure 4:
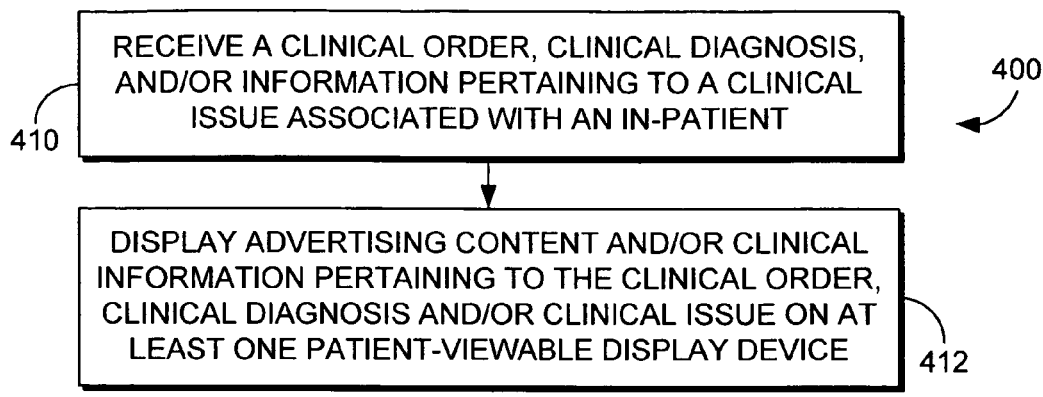
FIG. 4 is a flow diagram showing a method for displaying clinically-related advertising content and/or clinical information in accordance with an embodiment of the present invention.

Turning now to FIG. 4, a flow diagram is illustrated which shows a method 400 for displaying clinically-related advertising content and/or clinical information on at least one patient-viewable display device in accordance with an embodiment of the present invention. Such advertising content may include, by way of example only, advertising for a particular medication a patient has been scheduled to receive, which advertising may encourage the patient to select the name brand instead of the generic formulation of the medication. Clinical information may include, by way of example only, educational materials explaining procedures scheduled to be performed for the patient or setting forth the potential side effects of medications the patient is scheduled to receive, educational materials mandated by JCAHO requirements, support group information, and/or selectable links thereto.

Initially, as indicated at block 410, a clinical order, clinical diagnosis, and/or information pertaining to a clinical issue associated with a patient is received. Examples of each of these was discussed herein above with reference to FIGS. 2, 3A, and 3B. Subsequently, as indicated at block 412, advertising content (that is, clinically-related advertising content) and/or clinical information pertaining to the clinical order, clinical diagnosis, and/or clinical issue is displayed on at least one patient-viewable display device, for instance, a computing device monitor or the like.

Figure 5:
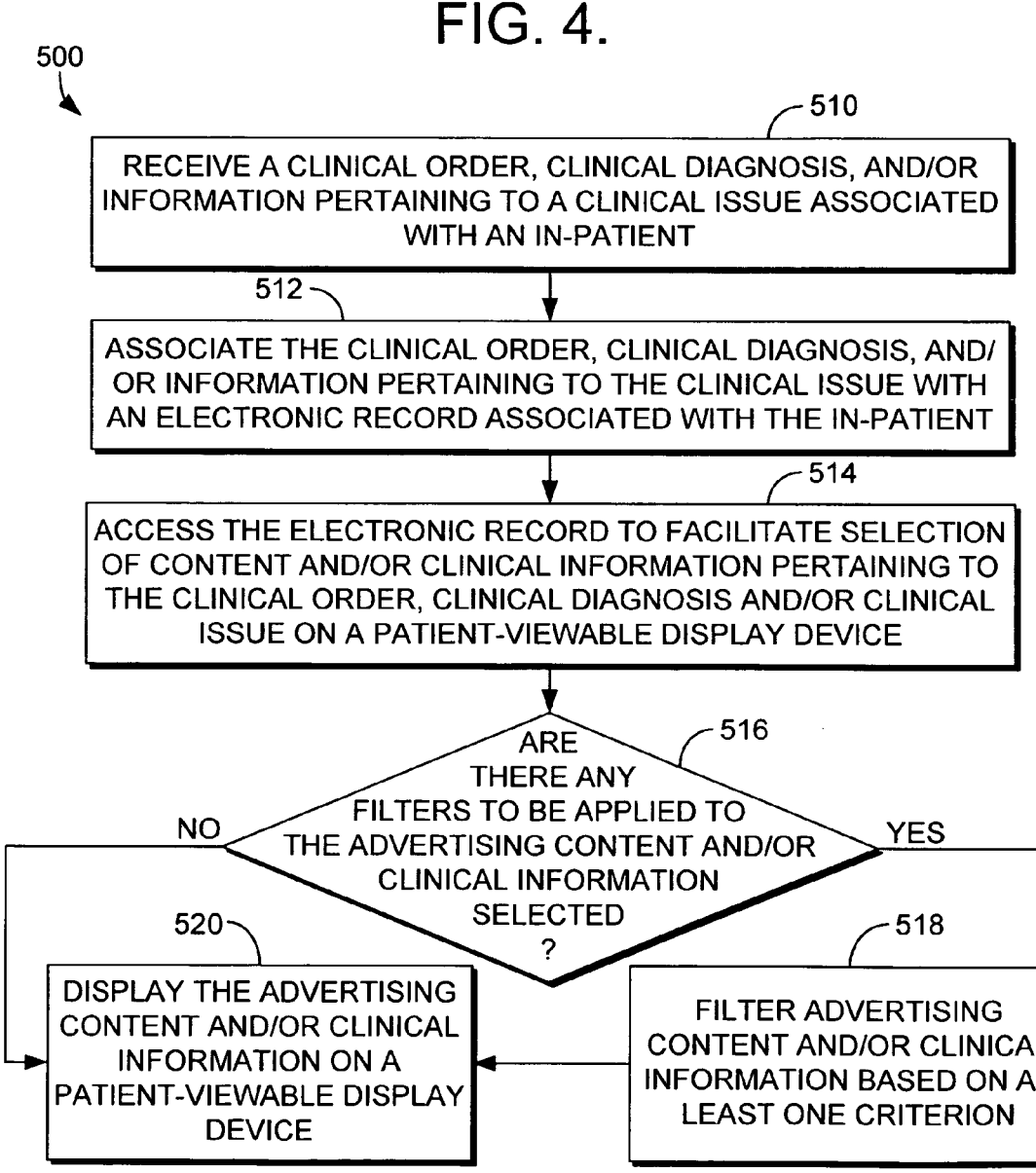
FIG. 5 is a flow diagram showing a more detailed method for displaying clinically-related advertising content and/or clinical information than the method of FIG. 4 in accordance with an embodiment of the present invention.

With reference to FIG. 5, a flow diagram is illustrated showing a more detailed method 500 for displaying clinically-related advertising content and/or clinical information than the method of FIG. 4 in accordance with an embodiment of the present invention. Initially, as indicated at block 510, a clinical order, clinical diagnosis, and/or information pertaining to a clinical issue associated with an in-patient is received. Subsequently, the clinical order, clinical diagnosis, and/or information pertaining to the clinical issue is associated with an electronic record associated with the in-patient, e.g., an electronic medical record, such as the POWERCHART application available from Cerner Corporation of North Kansas City, Miss. This is indicated at block 512. Subsequently, as indicated at block 514, the electronic record is accessed to obtain the clinical order, clinical diagnosis, and/or information pertaining to the clinical issue, the clinical order, clinical diagnosis, and/or information pertaining to the clinical issue is utilized to select clinically-related advertising content and/or clinical information for display, and the clinically-related advertising content and/or clinical information is displayed on at least one patient-viewable display device.

Next, it is determined whether there are any filters to be applied to the clinically-related advertising content and/or clinical information selected, as indicated at block 516. As previously described with respect to step 320 of FIG. 3A, such filters may set forth at least one care giver-specified criterion, in-patient-specified criterion, or institution-specified criterion. If any filters are to be applied, the advertising content and/or clinical information is subsequently filtered based on at least one criterion, as indicated at block 518. Subsequently, or if no filters are to be applied, the clinically-related advertising content and/or clinical information is displayed on at least one patient-viewable display device. This is indicated at block 520.

Figure 6A:
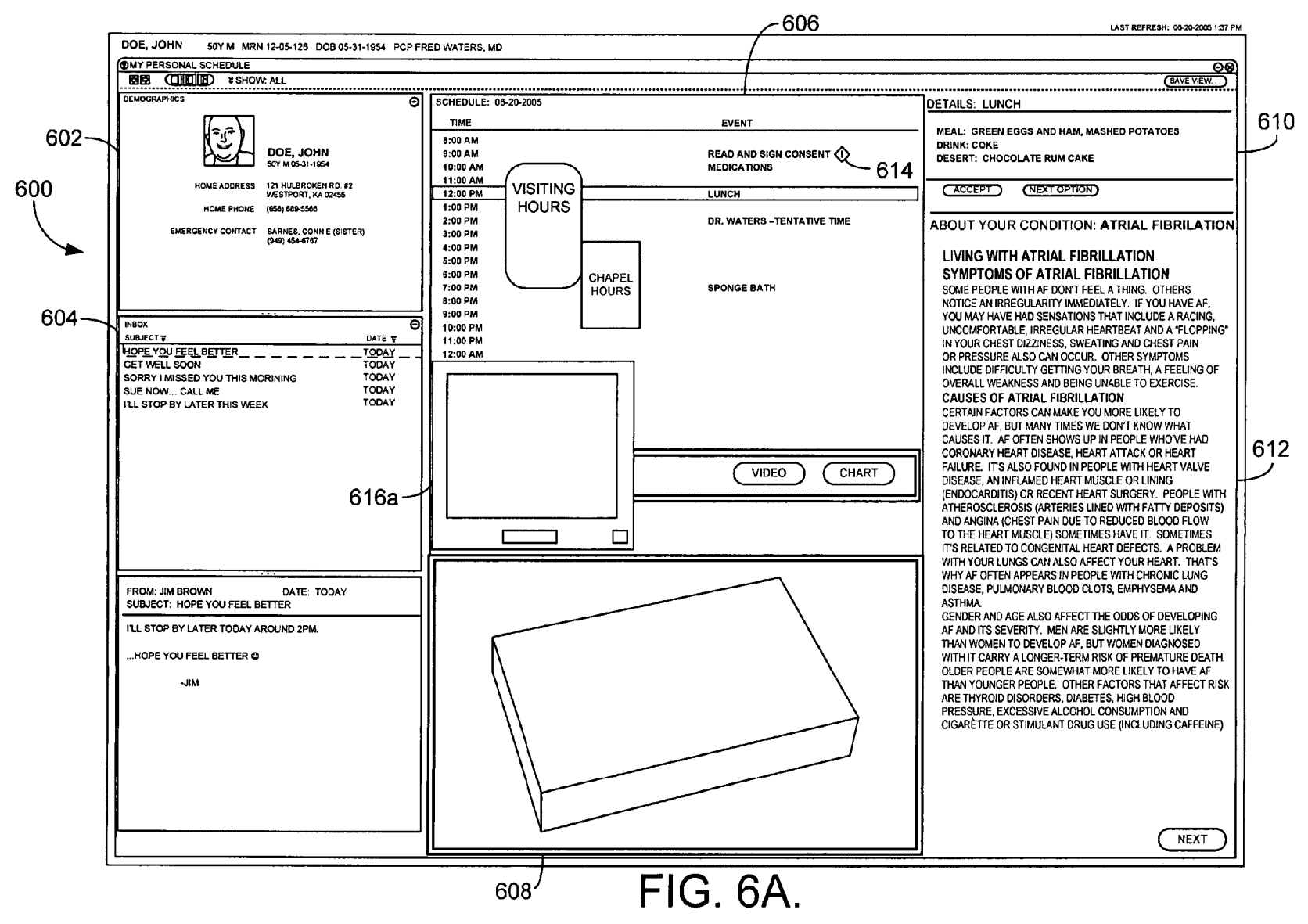

Turning now to FIG. 6A, an exemplary screen display illustrating display of clinically-related in-patient information on a patient-viewable display device, in accordance with an embodiment of the present invention, is illustrated and designated generally as reference numeral 600. It will be understood and appreciated by those of ordinary skill in the art that the screen display of FIG. 6A is provided by way of example only and it is not intended to limit the scope of the present invention in any way. Further, it will be understood and appreciated that the screen display 600 of FIG. 6A may be customized by the in-patient (or other authorized person) such that only those items which he or she wishes to view are displayed. All such variations are contemplated to be within the scope hereof.

Screen display 600 includes a demographics display area 602, an email display area 604, a schedule display area 606, an advertising content display area 608, a menu display area 610, and an additional information display area 612. The demographics display area 602 includes basic information about the in-patient to whom the displayed information pertains, such information being derived from an electronic record associated with the in-patient. For example, the demographics display area 602 includes the patient's name, age, date of birth, home address, home telephone number, and emergency contact information, in addition to a picture of the patient. The email display area 604 includes an inbox and a viewing area so that the patient can check his or her email, if desired. The schedule display area 606 includes clinically-related tasks that have been scheduled for the in-patient's day (in accordance with the above-described methods), as well as additional non-clinically-related scheduling information such as institution visiting hours and a chapel service schedule.

Note that one of the tasks on the patient's schedule includes an in-patient-action indicator 614 in the form of a diamond with an exclamation point inside. This indicator indicates that in-patient action is required on this particular task before, for instance, a particular procedure may be performed. It will be understood and appreciated by those of ordinary skill in the art that the particular form of the in-patient-action indicator is shown by way of example only and that any indicator serving to inform the in-patient and/or his or her loved ones that action is required is contemplated to be within the scope of the present invention.

The advertising content display area 608 includes any clinically-related advertising content that has been selected for the in-patient based upon the above-described methods. The menu display area 610 includes meal menu information and permits the in-patient to browse through options, if available, and select the meal of his or her choice, if appropriate. Systems and methods for user-centric (e.g., in-patient-centric) selection of menu options is more fully described below with reference to FIGS. 7A, 7B and 8A-8I. The additional information display area 612 includes information, in this case clinically-related information, for the patient to review, if desired. As previously discussed, such clinically-related information may include, by way of example only, educational materials explaining procedures scheduled to be performed for the in-patient or setting forth the potential side effects of medications the in-patient is scheduled to receive, educational materials mandated by JCAHO requirements, support group information, and/or selectable links thereto.

Figure 6B:
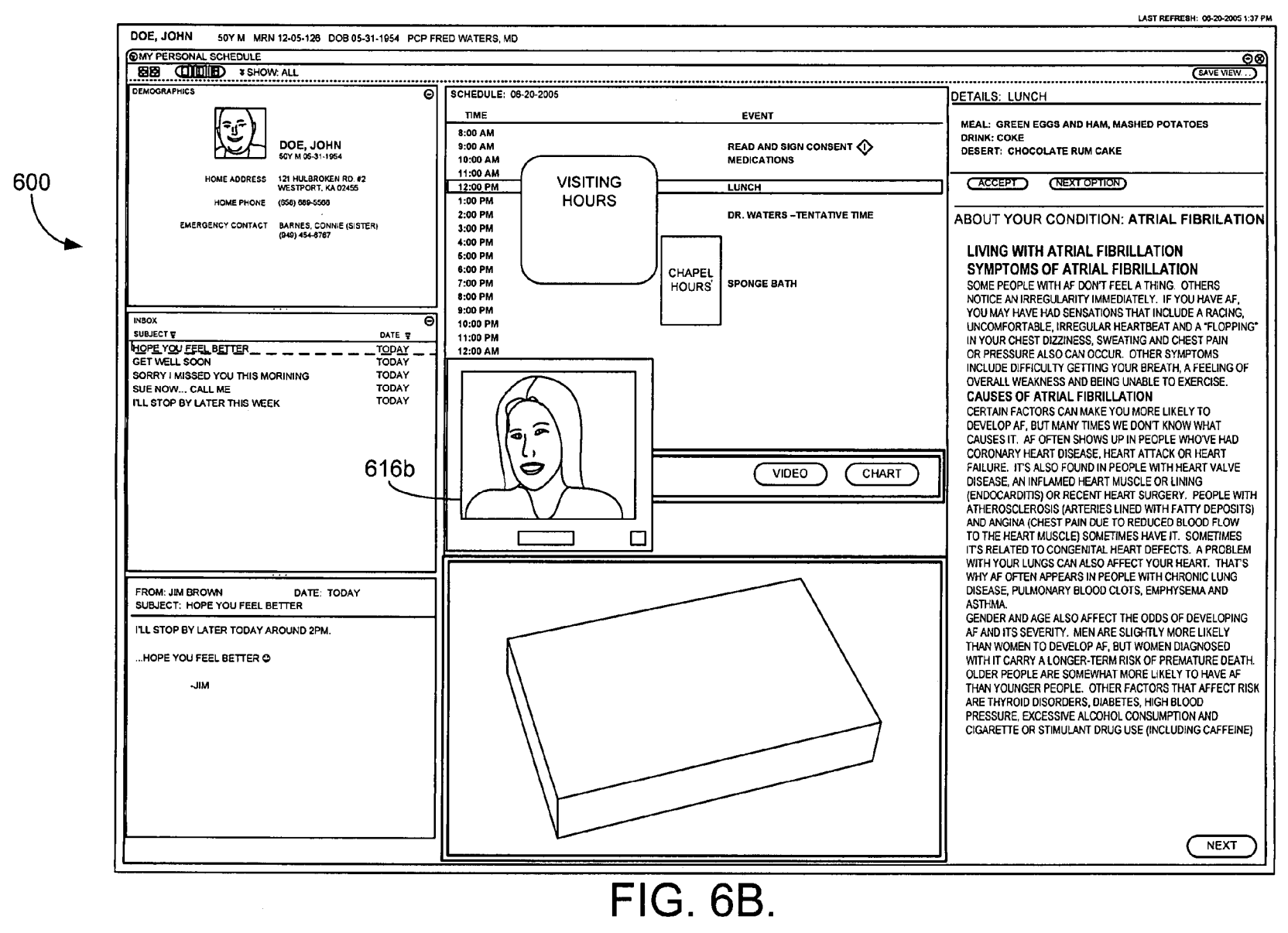

The screen display 600 of FIG. 6A additionally includes a live-connect display area 616a wherein the in-patient may view a connection established via an audio/video connection with another person in a remote location if appropriate capability is available. Such other person may be a family member or the like located at his or her residence, or may be another institution in-patient, e.g., the baby of an in-patient woman who has recently given birth. The live-connect display area 616a of FIG. 6A is not active. However, in the similar view of FIG. 6B, the live-connect display area 616b is illustrated showing a live connection.

In operation, by way of example only, suppose a diabetic patient presented to the emergency department of a particular institution complaining of chest pain and, after being examined, was admitted to the institution with an admitting diagnosis of Acute Myocardial Infarction (AMI). During the patient's stay, s/he underwent a Diagnostic Cardiac Catheterization yielding a diagnosis of 75% stenosis of the Mid-LAD, 85% stenosis of the proximal RCA, and 90% stenosis of the distal LAD. The patient, however, did not undergo an intervention due to the specific circumstances at the time. The intervention is accordingly scheduled for the following day. The patient is wheeled back to his or her room to recover from the Catheterization procedure. After recovering, the patient is interested in viewing information related to his/her stay to see what the next steps are along with what the available options are for dinner.

Upon accessing his/her information, an initial screen display appears, e.g., the screen display illustrated in FIG. 6A. The patient's calendar shows a range of two days displaying today's and tomorrow's schedule. The patient when s/he arrived back in the room and when the doctor is schedule to visit to review the procedure results. Further, the patient sees that s/he is scheduled for an intervention the following day at 9:00 am. On the right-hand side of the screen, is education information about coronary artery blockage (the patient's diagnosis). Further, they see educational information about interventional cardiac catheterization (the procedure s/he will be having the next day). A check box appears for the educational material providing the capability of capturing the fact that the patient acknowledged reading the material.

Also on the screen is the patient's dinner plan. The schedule shows it arriving at 7:00 pm. To the right, it shows a scheduled meal tailored for his/her diabetic needs. The electronic record associated with the patient had diabetes listed so the meal planning system was automatically triggered to provide only diabetic meals, as more fully described below. The patient sees that asparagus is listed for their meal. The patient, however, doesn't care for asparagus, so he selects the "Next Option" indicator which causes display of another diabetic-formulated meal. As soon as the patient sees an offering that s/he likes, s/he selects the "Accept" indicator which causes notification to be forwarded to the kitchen that the patient in Room 121 has requested a particular meal. Meal selection, including alternatives to the described scenario, is more fully described below with reference to FIGS. 7A, 7B and 8A-8I.

On the medications front, the patient has been prescribed Plavix to thin their blood. In addition to the Plavix blood thinning educational material being displayed, advertising content related to alternatives for blood thinners are also displayed on the screen.

The patient schedule indicates that the cardiologist will arrive in the room at 3:30 pm to review the results with the patient and family. When the cardiologist arrives, he is able to select the Diagnostic Cardiac Catheterization procedure shown on the schedule that had taken place at 10:00 am that morning. Upon selecting this item, the system asks the user to sign in with a logon and password. Once the cardiologist has input the appropriate information, the images of the procedure are available for display so that the cardiologist may discuss the findings and explain the interventional procedure that will be done the following day.

Figure 7A:
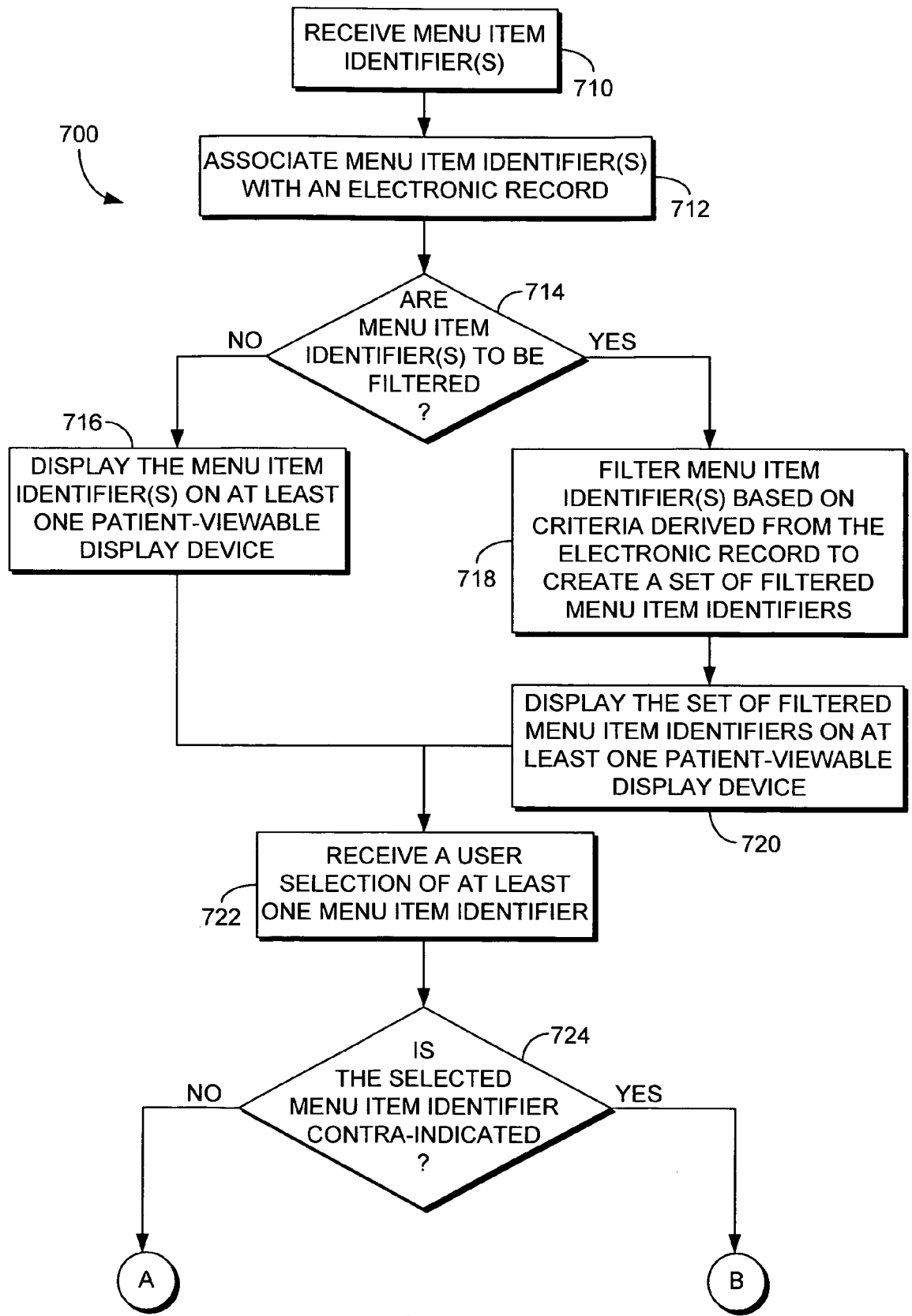
FIGS. 7A and 7B are a flow diagram showing a method for user-centric (e.g., in-patient-centric) selection of at least one menu item in accordance with an embodiment of the present invention.
Figure 7B:
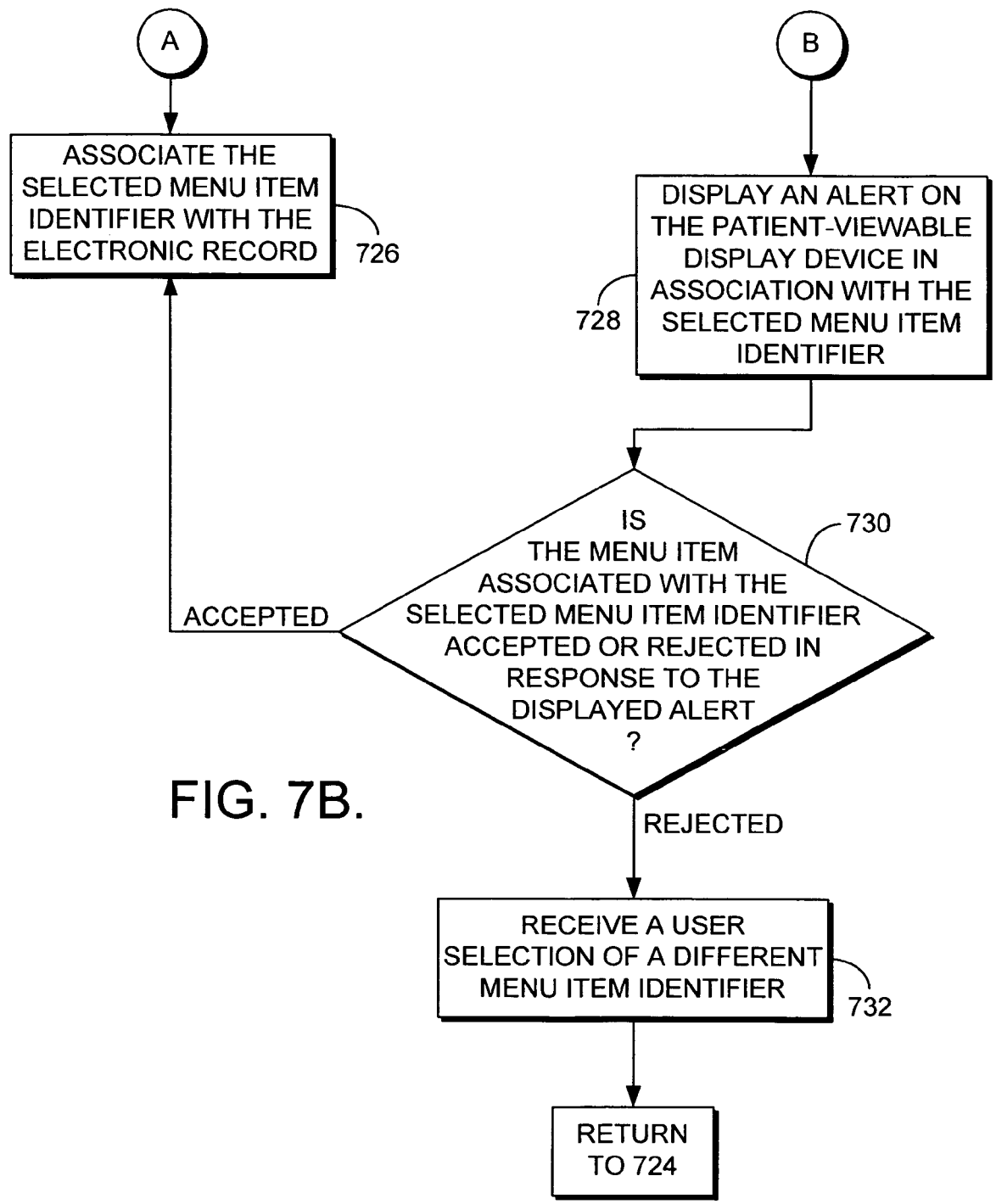

Turning now to FIGS. 7A and 7B, a flow diagram showing a method for user-centric selection of at least one menu item in accordance with an embodiment of the present invention is illustrated and depicted generally as reference numeral 700. Method 700 may be implemented on the above-described exemplary computing system environment (FIG. 1) and, by way of example only, may be utilized by an in-patient in a patient care institution to select desired menu items for consumption. As used herein, the term "user-centric" refers to the fact that a user, typically an in-patient, has at least partial control over the menu items s/he will be served by virtue of selections s/he makes, as more fully described below. However, the term "user-centric" is also intended to encompass menu item selections made by someone other than the in-patient themselves, e.g., a friend or family member of the in-patient, either from a patient-viewable display device or a remotely located display device having similar capabilities. Any and all variations thereof are contemplated to be within the scope of embodiments of the present invention.

Initially, as indicated at block 710, one or more menu item identifiers are received, each menu item identifier being associated with a particular menu item. Typically, each menu item identifier will be associated with a different menu item and will be descriptive thereof. For instance, the menu identifier "milk" may be associated with the menu item milk. Next, as indicated at block 712, each menu item identifier received is associated with an electronic record associated with an in-patient, e.g., an electronic medical record, such as the POWERCHART application available from Cerner Corporation of North Kansas City, Miss. By providing association with an electronic record, the menu item identifiers may be compared or verified against relevant medical information derived from the electronic record, as more fully described below.

Next, as indicated at block 714, it is determined whether or not the menu item identifiers are to be filtered based on at least one criterion derived from the electronic record. Filtering may be based upon a number of criteria including, but not limited to, the in-patient's diagnosis or condition, medications the in-patient may be taking, food allergies the in-patient may have, scheduled procedures, clinician's orders, and the like. Filtering the menu item identifiers based upon such criteria aids in ensuring that any menu item selections offered to the in-patient are safe for the in-patient to consume.

If it is determined at block 714 that the menu item identifiers are not to be filtered, all of the received menu item identifiers are displayed on at least one patient-viewable display device, as indicated at block 716. Note that in this instance, the in-patient may be able to view menu item identifiers that are available and yet contra-indicated for the particular in-patient. This scenario is more fully described below.

If, however, it is determined at block 714 that the menu item identifiers are to be filtered based on at least one criterion derived from the electronic record, the menu item identifiers are subsequently filtered based on the criterion (or criteria) to create a set of filtered menu item identifiers. This is indicated at block 718. Note that the "set" may include any number of menu item identifiers, including zero or one. Subsequently, as indicated at block 720, the set of filtered menu item identifiers is displayed on at least one patient-viewable display device. Note that in this instance, the in-patient is likely able to view only those menu item identifiers that are determined to be relatively safe for the particular in-patient to consume.

Next, as indicated at block 722, a user selection of at least one menu item identifier from the displayed identifiers is received. As discussed hereinabove, in one embodiment, the patient-viewable display device is a flat panel monitor having an interactive touch screen. In this embodiment, the in-patient may simply make his or her selection(s) by touching the display device screen with the selection(s) subsequently or simultaneously being received by the system. In additional embodiments, the selection(s) may be made by virtue of a mouse or the like, as known to those of ordinary skill in the art.

Subsequently, as indicated at block 724, it is determined whether or not any of the selected menu item identifiers are contra-indicated for the particular in-patient. A particular menu item identifier may be contra-indicated based largely on the same types of criteria derived from the in-patient's electronic record as filtering may be based upon (as discussed above with regard to blocks 714 and 718). Such criteria include, but are not limited to, the in-patient's diagnosis or condition, medications the in-patient may be taking, food allergies the in-patient may have, scheduled procedures, clinician's orders, and the like. Accordingly, such determination may be made by comparing the selected menu item identifiers with at least one criterion derived from the in-patient's electronic record.

In one embodiment, filtering (as indicated at block 714) and determining that a particular menu item identifier is contra-indicated will not both occur. That is, if the selected menu item identifiers are preemptively filtered, none of the menu item identifiers displayed on the patient-viewable display device (as shown at block 720) will be contra-indicated. Alternatively, if the selected menu item identifiers are not preemptively filtered, one or more of the menu item identifiers displayed on the patient-viewable display device (as shown at block 716) may be contra-indicated.

In another embodiment, however, a particular menu item identifier may be filtered based on one or more different criteria than the criterion or criteria that a contra-indication determination may be based upon. For instance, contemplate a scenario wherein the menu item identifiers received at block 710 are filtered based upon the in-patient's diagnosis or condition, medications the in-patient is taking, and clinician's orders to avoid certain menu items for one reason or another. Contemplate further that the in-patient also has a mild food allergy. It may in this instance be desirable to display the menu item to which the patient has an allergy and permit the in-patient to decide whether or not he or she desires to consume that item since any reaction thereto is likely to be relatively mild. As such, the menu item identifiers may not be filtered based upon the food allergy but rather determined to be contra-indicated (at block 724) if the in-patient selects to consume such item, as this scenario permits the in-patient to override the contra-indication, as more fully described below.

If it is determined at block 724 that the selected menu item identifier(s) are not contra-indicated, the menu item identifier(s) are subsequently associated with the in-patient's electronic record, as indicated at block 726. Once associated with the electronic record, the menu item(s) associated with the menu item identifier(s) are essentially "ordered" by the in-patient for the particular meal to which they pertain. Thus, the menu items associated with the menu item identifiers are patient-directed orders which are checked or verified against medically relevant information derived from the in-patient's electronic record. The identifiers for the "ordered" menu items may subsequently be displayed on the patient-viewable display device as a planned meal, if desired.

If, however, it is determined at block 724 that one or more of the selected menu item identifiers are contra-indicated, an alert may subsequently be displayed on the patient-viewable display device in association with the selected menu item identifier. This is indicated at block 728. In one embodiment, the displayed alert may simply alert the viewer that the item is contra-indicated but require further action, e.g., selecting to display a drop-down menu or the like, for the viewer to see the nature of the alert. In another embodiment, the displayed alert may itself indicate the nature thereof. Any and all such variations are contemplated to be within the scope of the present invention.

Subsequently, as indicated at block 730, it is determined whether the menu item associated with the selected menu item identifier is accepted or rejected in response to the displayed alert. That is, it is determined whether the in-patient (or other individual responsible for the in-patient's meal selections) desires to override the alert and accept the menu item despite the contra-indication or desires to reject the menu item and make a different selection. Such determination is made upon receipt of a user indication, such indication being input by the user utilizing a touch screen, mouse, or the like.

If it is determined that the in-patient desires to accept the menu item, the menu item identifier is associated with the in-patient's electronic record, as indicated at block 726. If, however, it is determined that the in-patient desires to reject the menu item in response to the displayed alert, a user selection of a different menu item identifier is subsequently received, as indicated at block 732. Such user selection may be received as indicated above with reference to block 722.

Once the different menu item identifier is received, the process returns to the step indicated at block 724 and repeated until a menu item associated with a selected menu item identifier is either not contra-indicated or contra-indicated and accepted by the user. Next, the selected menu item identifier is associated with the in-patient's electronic record, as indicated at block 726, and may be displayed on the patient-viewable display device as a planned meal, if desired.

In operation, suppose a patient, John Doe, is viewing his clinically-related in-patient information on the patient-viewable display device of FIG. 6A. As previously discussed, the screen display 600 of FIG. 6A includes a menu display area 610 wherein it is indicated that Mr. Doe is scheduled to receive green eggs and ham, mashed potatoes, coke and chocolate rum cake for lunch. If Mr. Doe wishes to receive the displayed meal, he may select the "Accept" indicator which causes notification to be forwarded to the kitchen that he has requested the displayed meal. However, if he wishes to receive an alternative lunch meal, in one embodiment, he may select the "Next Option" indicator to display a different meal option, selecting the "Accept" indicator when an acceptable lunch meal selection is displayed. In another embodiment, selection of the "Next Option" indicator may launch a dialog box which permits Mr. Doe to mix and match menu items to create his own lunch meal. This embodiment, is illustrated in FIGS. 8A-8I.

Figure 8A:
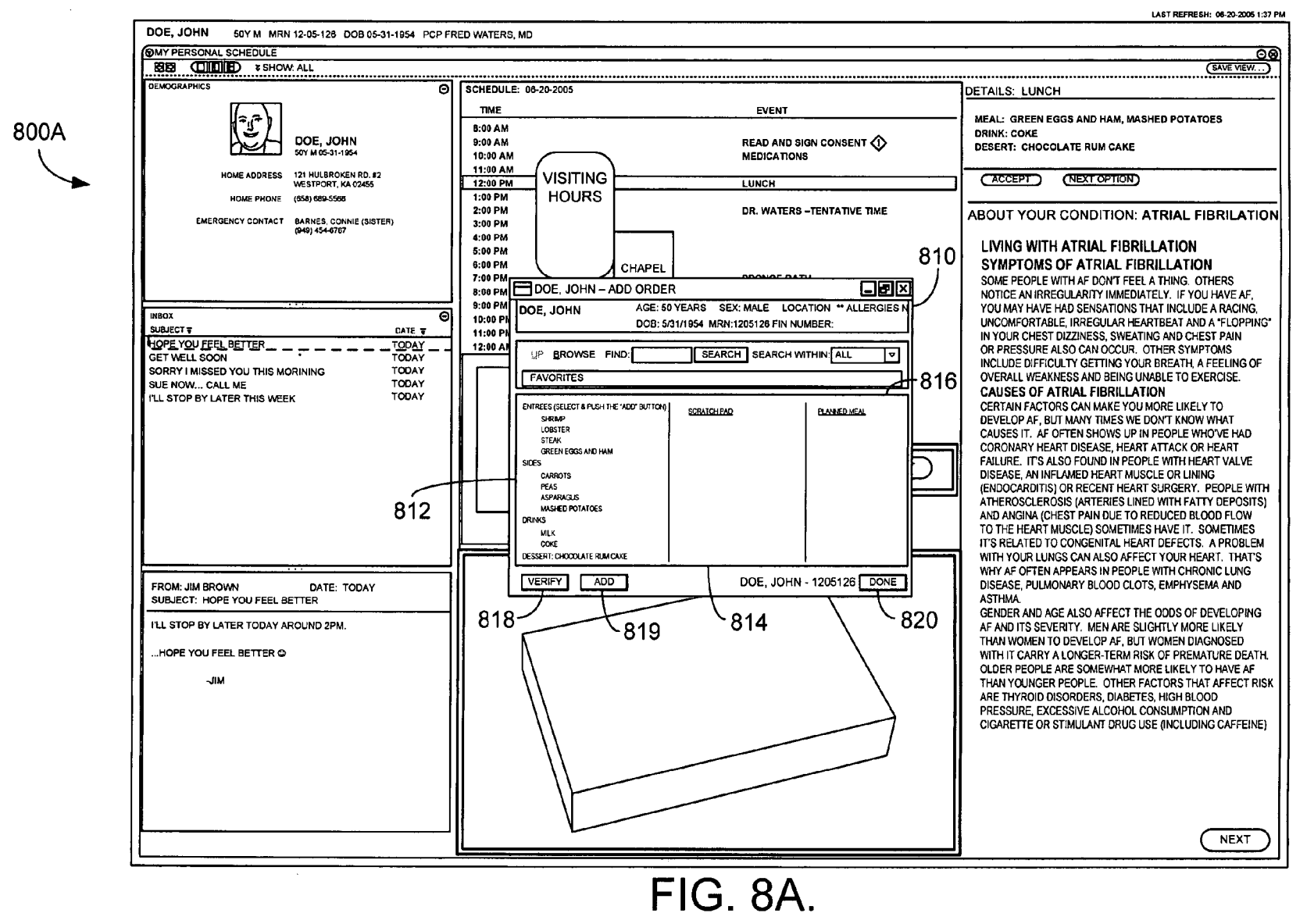

With reference to FIG. 8A, an exemplary screen display illustrating a dialog box 810 for selection of at least one menu item from a list of available menu item options is shown and designated generally as reference numeral 800A. The dialog box 810 includes an available menu item identifier display portion 812, a scratch pad portion 814, and a planned meal portion 816. In the available menu item identifier display portion 812, identifiers for all menu items available for selection are displayed. It should be noted that if the menu item identifier(s) received at step 710 of FIG. 7A have been filtered (as indicated at step 714), the available menu item identifier display portion 812 displays the set of filtered menu item identifiers rather than all menu item identifiers received. The scratch pad portion 814 will display those menu items selected by Mr. Doe, as more fully described below. As also more fully described below, the planned meal display portion 816 will display the planned meal once such planned meal has been determined.

The screen display 800A additionally includes a "verify" indicator 818, an "add" indicator 819, and a "done" indicator 820. Selection of the "verify" indicator 818 initiates the determination whether or not any of the selected menu item identifiers are contra-indicated. Selection of the "add" indicator 819 causes a selected menu item to be copied from the available menu item identifier display portion 812 to the scratch pad portion 814. Selection of the "done" indicator 820 causes menu item identifiers displayed in the scratch pad portion 814 to be transferred to the planned meal portion 816 and/or causes the dialog box 810 to be closed and the planned meal to be displayed in the menu display area (610 of FIG. 6A), as appropriate. Each of these indicators, and the functions performed upon selection thereof, is more fully described below.

Figure 8B:
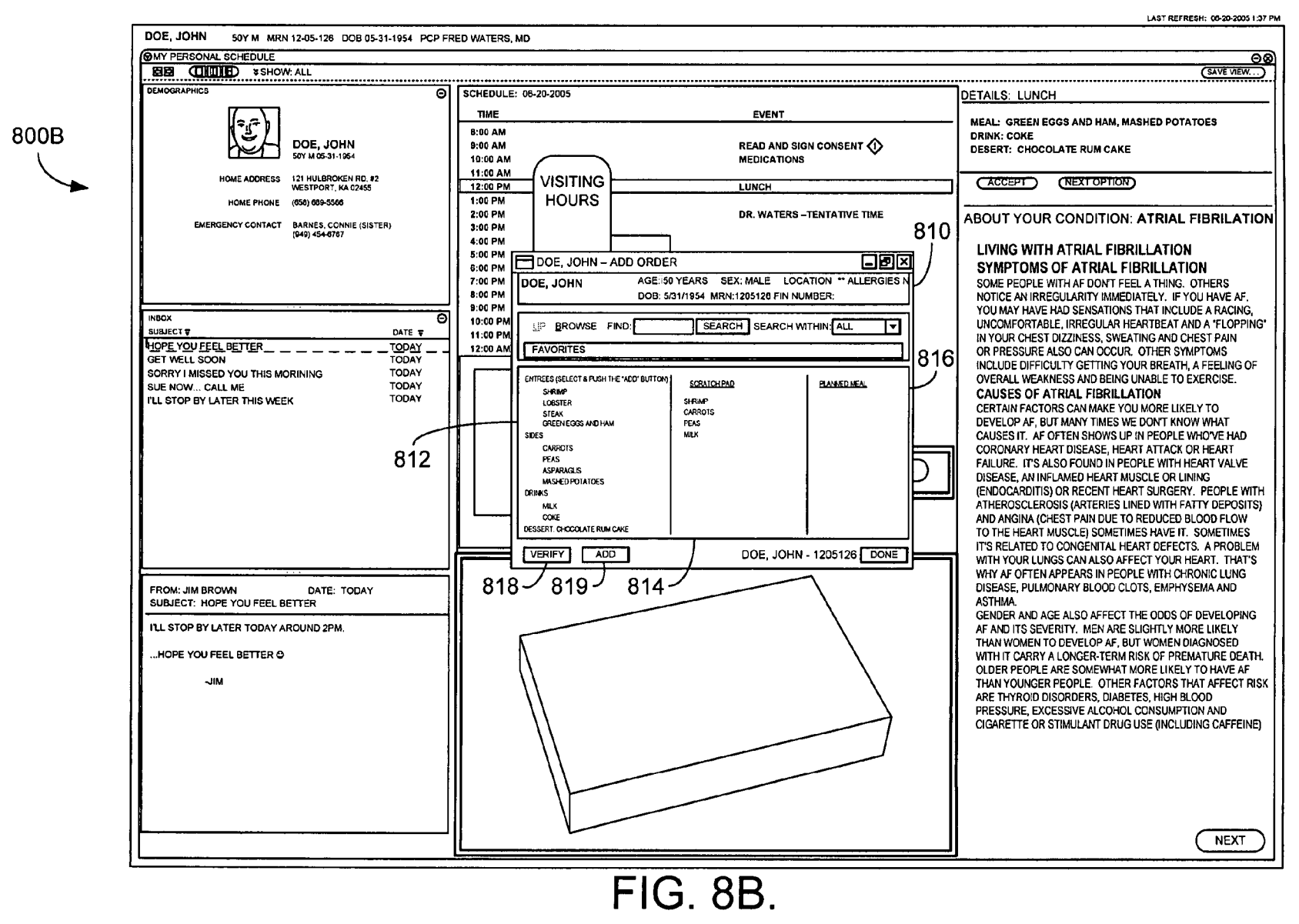

Returning to the above-described exemplary scenario, contemplate that Mr. Doe desires to consume shrimp, carrots, peas and milk for his lunch meal instead of green eggs and ham, mashed potatoes, coke, and chocolate rum cake. Upon display of the dialog box 810, Mr. Doe may select each desired menu item from the available menu item identifier display portion 812 followed by the "add" indicator 819 to add the items to the scratch pad portion 814 of the dialog box 810. FIG. 8B shows an exemplary screen display 800B illustrating such action by Mr. Doe has taken place. Subsequent to such selections being made, Mr. Doe may select the "verify" indicator 818 to determine if any of the selected menu item identifiers are contra-indicated for Mr. Doe.

Figure 8C:
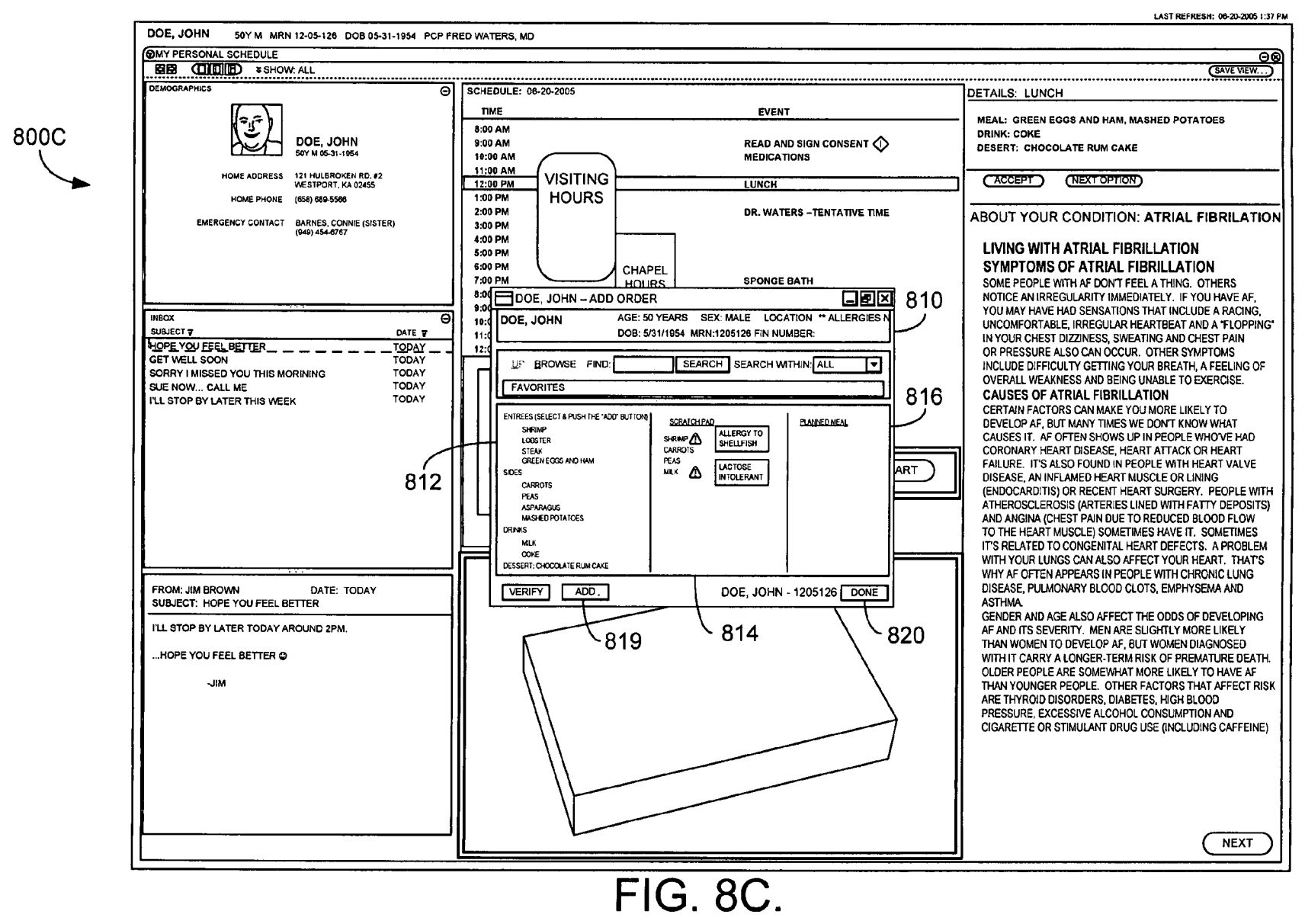

FIG. 8C shows an exemplary screen display 800C illustrating that Mr. Doe has selected the "verify" indicator 818 and both shrimp and milk have been determined to be contra-indicated for him. Accordingly, alerts are displayed in association with each of the menu item identifiers "shrimp" and "milk" in the scratch pad portion 814. In the illustrated embodiment, the alert additionally indicates the nature thereof indicating that Mr. Doe has an allergy to shellfish and is lactose intolerant.

Figure 8D:
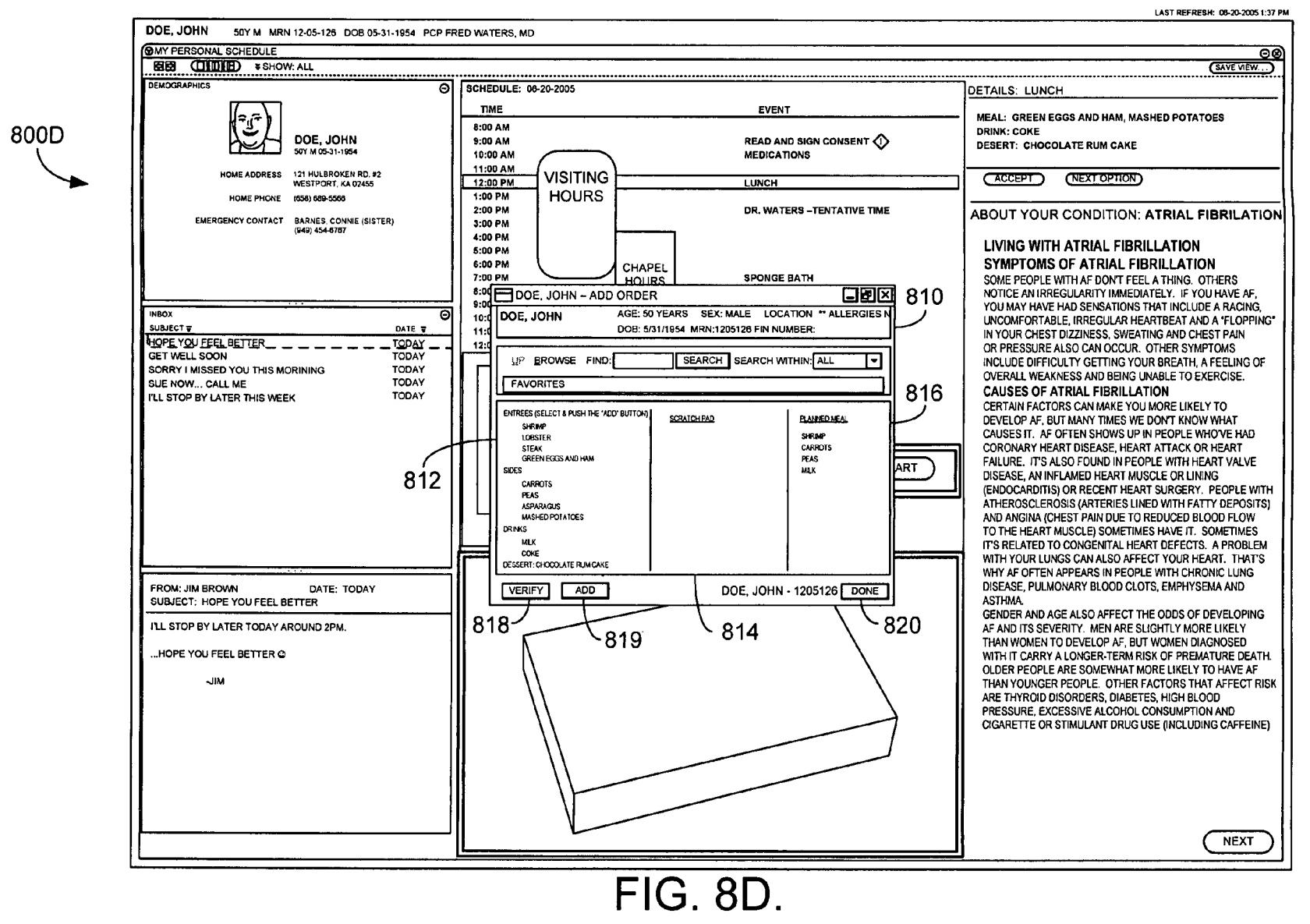

Mr. Doe now has the choice to either accept or reject any or all of the menu items for which menu item identifiers are displayed in the scratch pad portion 814, particularly those which have been determined to be contra-indicated (e.g., shrimp and milk). If Mr. Doe desires to accept the menu items despite the displayed alerts, he may select the "done" indicator 820. Such action removes the menu item identifiers and displayed alerts from the scratch pad portion 814 and causes them to instead be displayed in the planned meal portion 816. FIG. 8D shows an exemplary screen display 800D illustrating such action by Mr. Doe has taken place.

Figure 8E:
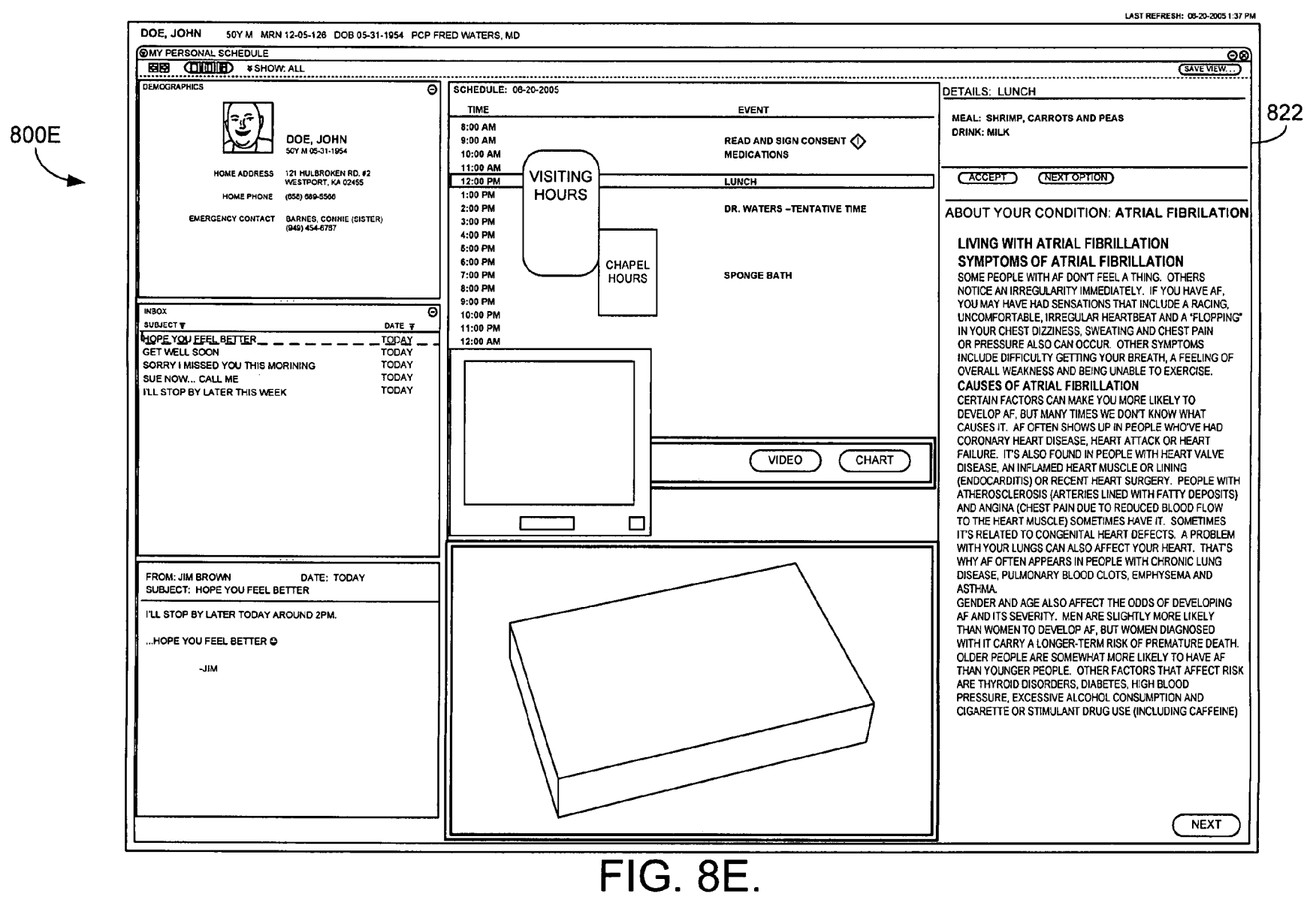

Subsequent to such action taking place, Mr. Doe may select the "done" indicator 820 a second time to cause the dialog box 810 to be closed. In one embodiment, upon closing of the dialog box 810, the planned meal may be displayed in a menu display area 822 of the resultant screen display. FIG. 8E shows an exemplary screen display 800E illustrating such embodiment.

Figure 8F:
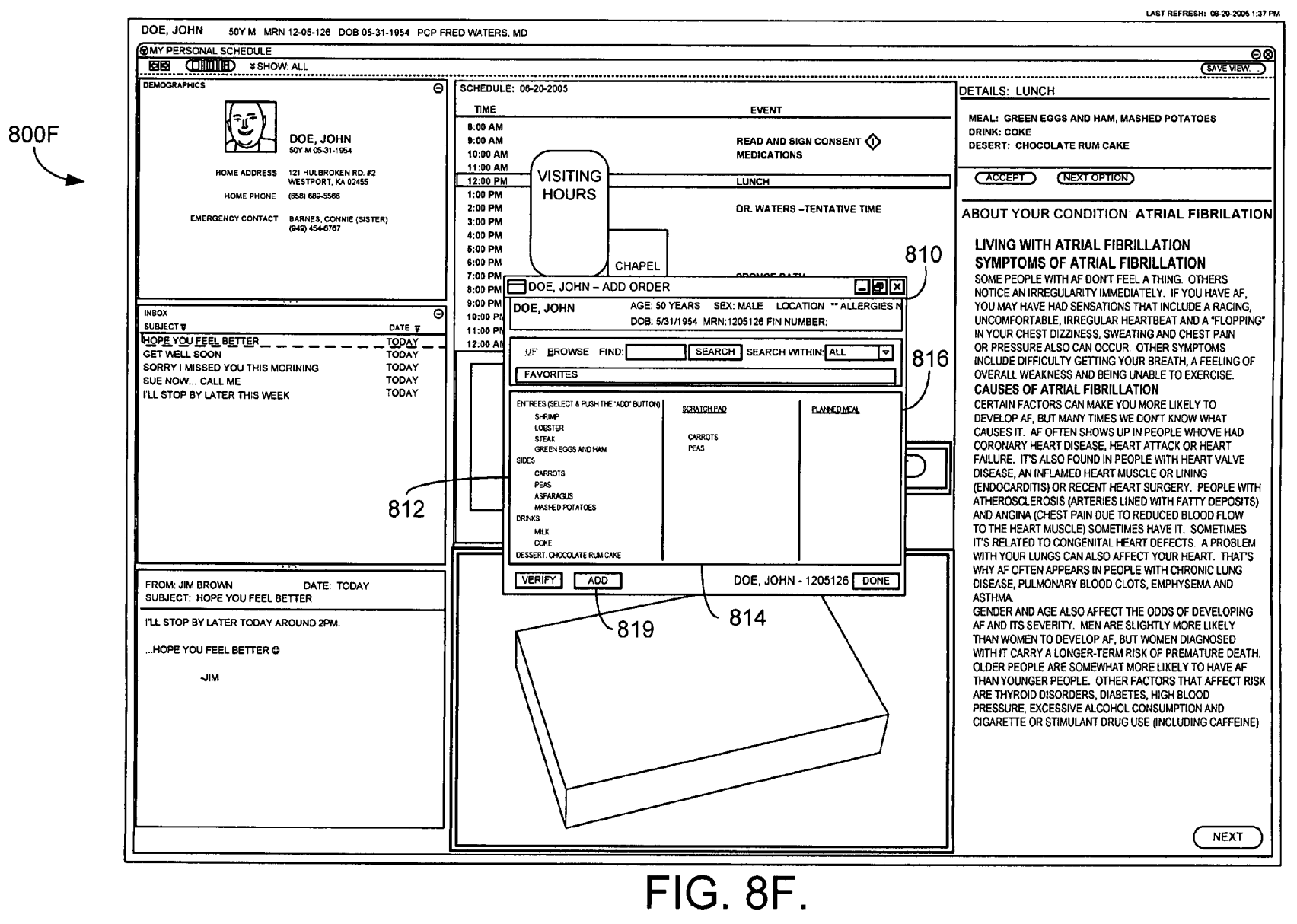

Returning to the screen display 800C shown in FIG. 8C if, Mr. Doe desires to reject any of the menu items for which menu item identifiers are displayed in the scratch pad portion 814 (particularly one or more of those which have been determined to be contra-indicated), he may remove the menu item identifier(s) from the scratch pad portion 814 and, if desired, make a different menu item selection. An exemplary screen display 800F illustrating that Mr. Doe has chosen to reject both shrimp and milk as menu item selections is shown in FIG. 8F. Removal of menu item identifiers from the scratch pad portion 814 may be accomplished in any number of ways including, but not limited to, dragging the appropriate menu item identifier from the scratch pad portion 814 to the available menu item identifier display portion 812 or selecting the menu item identifier in the scratch pad portion 814 to cause display of a drop-down menu having a "remove" or "cancel" selection available. Upon removal of a menu item identifier from the scratch pad portion 814 which has an alert associated therewith, both the menu item identifier and the alert are removed from the scratch pad portion 814.

Figure 8G:
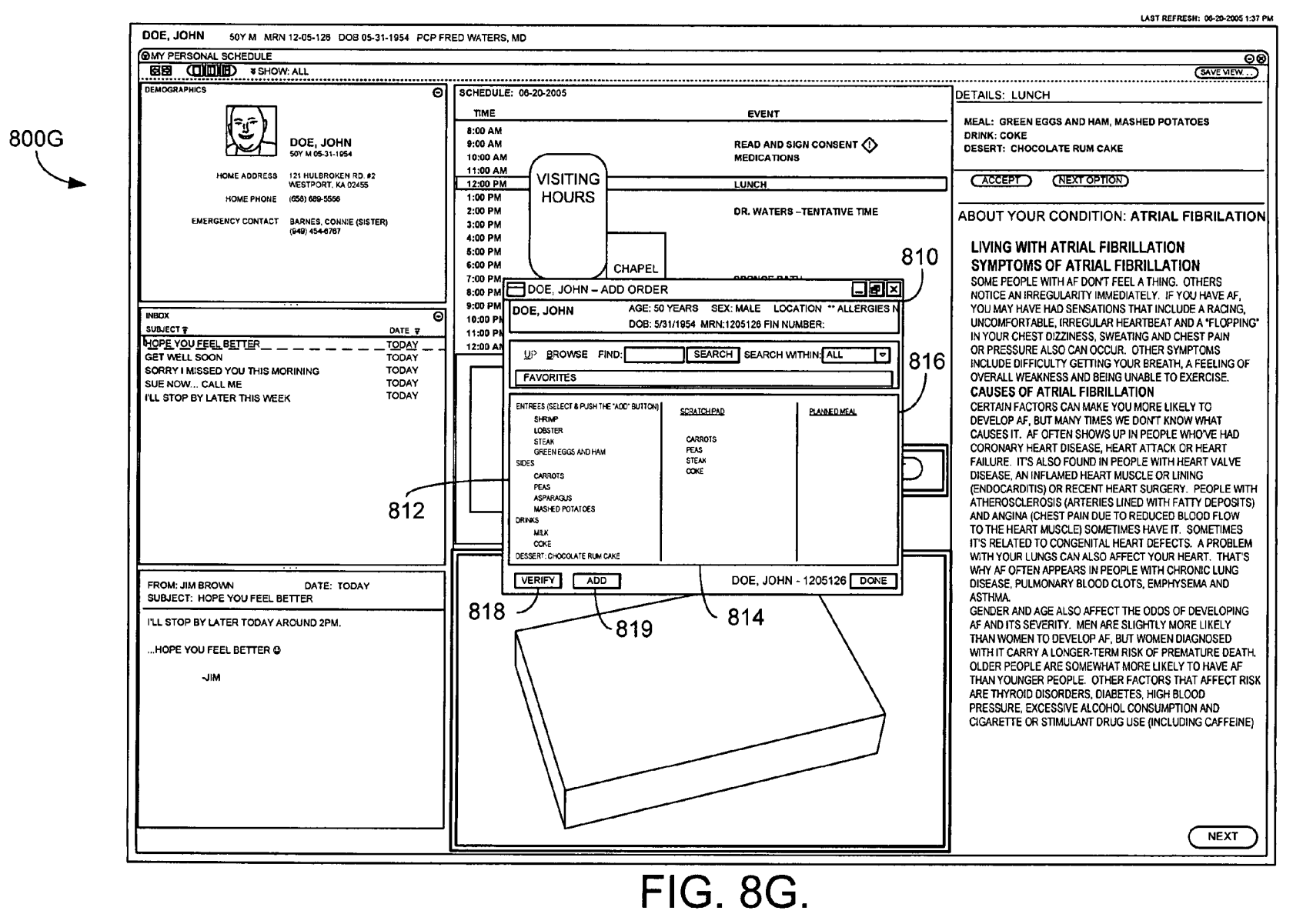

Upon rejection and/or removal of one or more of the menu item identifiers displayed in the scratch pad portion 814, Mr. Doe has the option of selecting a different menu item identifier(s) to replace the removed identifiers(s). An exemplary screen display 800G indicating that Mr. Doe has chosen to replace shrimp and milk with steak and coke is illustrated in FIG. 8G. Subsequent to such selections being made, Mr. Doe may again select the "verify" indicator 818 to determine if any of the menu item identifiers now displayed in the scratch pad portion 814 are contra-indicated.

Figure 8H:
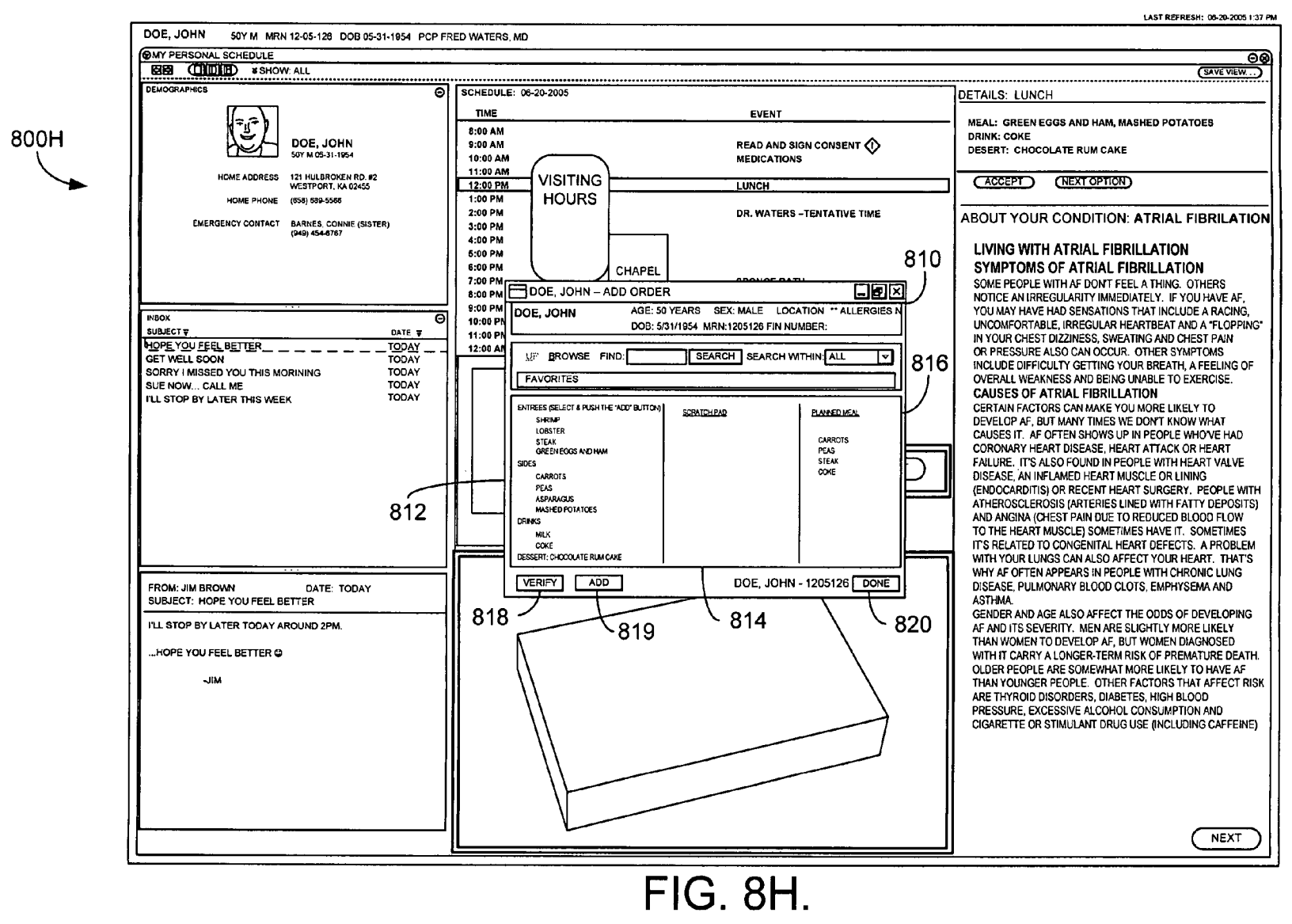

In the illustrated scenario, contemplate that none of the menu item identifiers now displayed in the scratch pad portion 814 is contra-indicated for Mr. Doe. As such, upon selection of the "verify" indicator 818, the menu item identifiers displayed in the scratch pad portion 814 may be removed from the scratch pad portion 814 and instead displayed in the planned meal portion 816. FIG. 8H shows an exemplary screen display 800H illustrating such action has taken place.

Figure 8I:
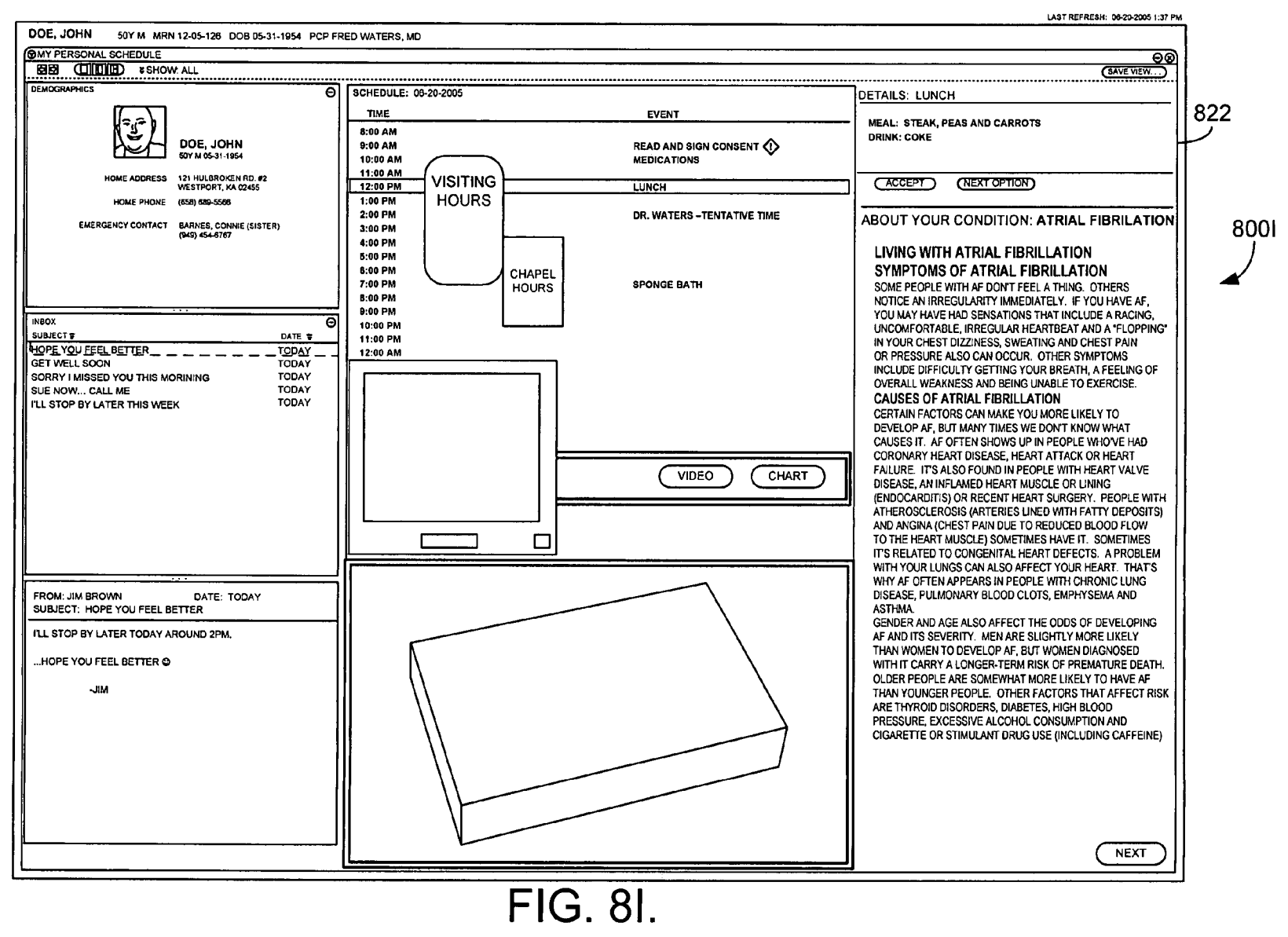

Subsequent to such action taking place, Mr. Doe may select the "done" indicator 820 to cause the dialog box 810 to be closed. In one embodiment, upon closing of the dialog box 810, the planned meal may be displayed in a menu display area 822 of the resultant screen display. FIG. 8I shows an exemplary screen display 800I illustrating such embodiment.

Note that had Mr. Doe chosen not to make any additional or different menu item identifier selections subsequent to the contra-indicated and rejected items being removed from the scratch pad portion 814 of the dialog box 810, he may have simply selected the "done" indicator 820 causing the planned meal to consist only of the menu items associated with the menu item identifiers which remained in the scratch pad portion 814 (i.e., carrots and peas).

As can be understood, the present invention provides methods and systems for use in, e.g., an in-patient care computing environment, the methods and systems for displaying clinically-related in-patient information on at least one patient-viewable display device. Utilizing the methods and systems described herein, in-patients and their loved ones are able to more actively participate in the selection of the menu items which they are scheduled to consume in a way that permits them to have an increased feeling of control over the care being received. This, in turn, not only provides for increased safety but leads to a more contented in-patient stay.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and sub-combinations are of utility and may be employed without reference to other features and sub-combinations. This is contemplated by and is within the scope of the claims.

What is claimed is:

1. Non-transitory computer-readable storage media having computer-executable instructions stored thereon that, when executed by a computing device, cause the computing device to perform a method of user-centric selection of a menu item, the method comprising:
   receiving a menu-item identifier that identifies a food item, which is available to be served to an in-patient;
   associating the menu-item identifier with an electronic record of the in-patient, wherein the electronic record indicates a condition of the patient that prohibits the in-patient from consuming a particular food item;
   prior to presenting the menu-item identifier to the in-patient, determining that the food item does not include the particular food item;
   displaying the menu-item identifier in a first portion of a patient-viewable display device, wherein the first portion is designated to present food items that are available to be served to the in-patient and that have not yet been selected to be included in a meal of the in-patient;
   receiving a user selection of the menu-item identifier,
   wherein, in response to receiving the user selection, the menu-item identifier is displayed in a second portion of the patient-viewable display device, the second portion being presented simultaneously with the first portion, and
   wherein the second portion is designated to present food items that are available to be served to the in-patient and that have been selected to be included in the meal;
   comparing by the processing device the menu-item identifier to an allergy of the in-patient to determine that the food item is contra-indicated for the inpatient;
   responsive to determining that the food item is contra-indicated, displaying an alert on the patient-viewable display device that indicates the food item is contra-indicated, wherein the alert is displayed in the second portion adjacent to the menu-item identifier that is displayed in the second portion;
   receiving input indicating an acceptance of the menu-item identifier despite the food item being contra-indicated; and
   responsive to receiving the input indicating the acceptance, displaying the menu-item identifier in a third portion of the patient-viewable display device,
   wherein the third portion is designated to present food items that will be included in the meal of the in-patient, and
   wherein the third portion is presented simultaneously with the first portion and the second portion.

2. The non-transitory computer-readable storage media of claim 1, further comprising associating the user selection of the menu-item identifier with the electronic record associated with the inpatient.

3. The non-transitory computer-readable storage media of claim 1, wherein when it is determined that the food item identified by the menu-item identifier is not contra-indicated, the method further comprises associating the user selection of the menu item identifier with the electronic record associated with the inpatient.

4. The non-transitory computer-readable storage media of claim 1 wherein, when the input indicates a rejection of the food item, the method further comprises receiving a user selection of a second menu-item identifier that identifies an alternative food item.

5. A computer-implemented method, which is implemented using a processing device, a computer storage device, or a combination thereof, for user-centric selection of at least one menu item, the method comprising:
  receiving a menu-item identifier that identifies a food item, which is available to be served to an in-patient and has not been selected to be included in a meal of the in-patient;
  associating by the processing device the menu-item identifier with an electronic record of the in-patient,
  wherein the electronic record includes a condition, a medication, or a combination thereof that prohibits the in-patient from consuming a particular food item;
  prior to presenting the menu-item identifier to the in-patient, comparing by the processing device the menu-item identifier to the particular food item to determine that the in-patient is not prohibited from consuming the food item;
  displaying the menu-item identifier in a first portion of a patient-viewable display device;
  receiving a user selection of the menu-item identifier, wherein, in response to receiving the user selection, the menu-item identifier is displayed in a second portion of the patient-viewable display device, the second portion being presented simultaneously with the first portion;
  comparing by the processing device the menu-item identifier to an allergy of the in-patient to determine that the food item is contra-indicated for the inpatient;
  responsive to determining that the food item is contra-indicated, displaying an alert on the patient-viewable display device that indicates the food item is contra-indicated, wherein the alert is displayed in the second portion;
  receiving input indicating an acceptance of the menu-item identifier despite the food item being contra-indicated; and
  responsive to receiving the input indicating the acceptance, displaying the menu-item identifier in a third portion of the patient-viewable display device, wherein the third portion is presented simultaneously with the first portion and the second portion.

6. A system stored on non-transitory computer-readable storage media for user-centric selection of at least one menu item, the system comprising:
  a menu-item-identifier receiving module that receives a menu-item identifier, which describes a food item that is available to be served to an in-patient;
  an associating module that associates the menu-item identifier with an electronic record associated with an in-patient;
  a displaying module that displays the menu-item identifier in a first portion of a patient-viewable display device, wherein the first portion is designated to present menu items that are available to be served to the in-patient and that have not yet been selected to be included in a meal of the in-patient;
  a user-selection receiving module that receives a first user selection of the menu-item identifier,
  wherein, in response to the user-selection receiving module receiving the first user selection, the displaying module displays the menu-item identifier in a second portion of the patient-viewable display device, the second portion being presented simultaneously with the first portion, and
  wherein the second portion is designated to present food items that are available to be served to the in-patient and that have been selected to be included in the meal;
  a comparing module that compares the menu-item identifier to a criterion derived from the electronic record, wherein comparing the menu-item identifier to the criterion indicates that the menu item is contra-indicated for the in-patient;
  an alert-generating module that, responsive to the first-menu item being contra-indicated, generates an alert that indicates the food item is contra-indicated, wherein the displaying module displays the alert in the second portion adjacent to the menu-item identifier that is also displayed in the second portion; and
  a second user-selection receiving module that, after the menu-item identifier is displayed together with the alert, receives a second user selection of the menu-item identifier, thereby overriding the alert,
  wherein responsive to receiving the second user selection the displaying module displays the menu-item identifier in a third portion of the patient-viewable display device, and
  wherein the third portion is presented simultaneously with the first portion and the second portion.

7. The system of claim 6, further comprising a filtering module for filtering the plurality of menu item identifiers based on at least one criterion derived from the electronic record to create a set of filtered menu item identifiers.

* * * * *